US007385039B2

(12) United States Patent
Prell

(10) Patent No.: US 7,385,039 B2
(45) Date of Patent: Jun. 10, 2008

(54) METHODS AND COMPOSITIONS FOR REGULATING IMIDAZOLINE RECEPTORS

(76) Inventor: George Prell, 17 Fairmont Ave., Upper Montclair, NJ (US) 07043

( * ) Notice: Subject to any disclaimer, the term of this patent is extended or adjusted under 35 U.S.C. 154(b) by 136 days.

(21) Appl. No.: 10/937,938

(22) Filed: Sep. 11, 2004

(65) Prior Publication Data

US 2005/0137149 A1    Jun. 23, 2005

Related U.S. Application Data

(60) Continuation-in-part of application No. 10/918,942, filed on Aug. 16, 2004, now abandoned, which is a division of application No. 09/353,670, filed on Jul. 15, 1999, now Pat. No. 6,777,394.

(60) Provisional application No. 60/092,945, filed on Jul. 15, 1998.

(51) Int. Cl.
*C07K 16/44* (2006.01)
*A61K 39/395* (2006.01)

(52) U.S. Cl. .................................. 530/389.8; 424/175.1
(58) Field of Classification Search ...................... None
See application file for complete search history.

(56) References Cited

U.S. PATENT DOCUMENTS

| 5,681,947 A | 10/1997 | Bergstrom et al. |
| 6,777,394 B1 * | 8/2004 | Prell ............................ 514/43 |

FOREIGN PATENT DOCUMENTS

| DE | 3446894 | 12/1984 |
| GB | 2121799 | 6/1983 |
| HU | 36475 | 9/1985 |

OTHER PUBLICATIONS

Dontenwill, et al. A Circulating Substance Cross-reacting with Antiimidazoline Antibodies, J Clin Invest. 1993; 92:1068-1072.*
Prell, et al. Imidazoleacetic acid-ribotide, and endogenous imidazoline I1 receptor ligand. Society for Neuroscience Abstracts. 1998; 24(1-2):627.*

(Continued)

*Primary Examiner*—Mary R Mosher
*Assistant Examiner*—Stuart W Snyder
(74) *Attorney, Agent, or Firm*—Baker Botts LLP

(57) ABSTRACT

The present invention relates to methods and compositions for regulating the activity of imidazoline receptors. In particular, the invention relates to pharmaceutical compositions comprising imidazoleacetic acid-ribotide (IAA-RP), imidazoleacetic acid-riboside (IAA-R) and its related congeners such as pros-linked ribotide and riboside. The invention is based on the discovery that IAA-RP and to a lesser extent IAA-P bind with a high affinity to imidazoline receptors. Antibodies to IAA-RP and IAA-R are additionally provided, as well as screening methods for identification of compounds that either promote or antagonize the activity of IAA-RP, IAA-R and its related congeners. The invention further relates to diagnostic and prognostic methods for detection of abnormalities in levels or activity of IAA-RP and IAA-R. The invention encompasses treatment of disorders related to the imidazoline system, including hypertension, glaucoma, psychiatric (e.g., depression), neurological (e.g., motor disorders, neurodegenerative disorders), diabetes and disorders related to platelet aggregation.

2 Claims, 8 Drawing Sheets

Figure 1:
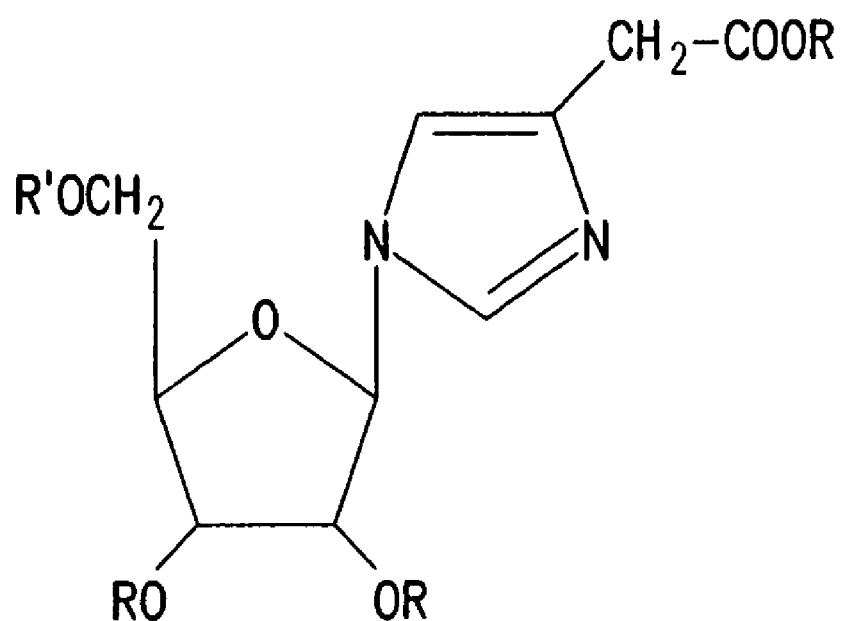

R=H, R'=PO$_3$H$_2$  IMIDAZOLEACETIC ACID-RIBOTIDE
R=R'=H  IMIDAZOLEACETIC ACID-RIBOSIDE

OTHER PUBLICATIONS

Prell et al. 1998, Imidazoleacetic acid-ribotide, an endogenous imidazoline II receptor ligand. Soc Neurosci Abst. 24:627; Abstract #246.18.*

Prell et al. 2003, Imidazoleacetic acid-Ribotide is an endogenous imidazoline receptor (IR) ligand. Presentation at 4th Intl Symposium on Agmatine and Imidazoline Systems, Abstract #T21; San Diego, CA Apr. 9-11, 2003.*

Prell et al 2004 Imidazoleacetic acid-ribotide: An endogenous ligand that stimulates imidazol(in)e receptors Proc Natl Acad Sci USA 101:13677-13682.*

Friedrich, et al. Distribution and cellular localization of imidazoleacetic acid-ribotide, an endogenous ligand at imidazo(in)e and adrenergic receptors, in rat brain. J. Chem. Neuroanat.(Netherlands) 2007; 33(1):53-64.*

Prell et al. 2004 Imidazoleacetic acid-ribotide: An endogenous ligand that stimulates imidazol(in)e receptors Proc Natl Acad Sci USA 101:13677-13682.

Prell et al. 2003, Imidazoleacetic acid-Ribotide is an endogenous imidazoline receptor (IR) ligand. Presentation at 4th Intl Symposium on Agmatine and Imidazoline Systems, Abstract #T21; San Diego, CA Apr. 9-11, 2003.

Eglen RM 1998, 'Seeing through a glass darkly': casting light on imidazoline 'I' sites. Trends in Pharmacol.Sci 19:381-390.

Prell et al. 1998, Imidazoleacetic acid-ribotide, an endogenous imidazoline I1 receptor ligand. Soc Neurosci Abst. 24:627; Abstract #246.18.

Barrow et al. 1997 Isolation of an endogenous clonidine-displacing substance from bovine lung and brain. Intl Workshop on Imidazoline receptors, Satellite Meeting to the Intl. Soc. of Autonomic Neurosciences, Melbourne Australia, Sep. 10, 1997.

Chan et al., 1997, The effect of the putative endogenous imidazoline receptor ligand, clonidine-displacing substance, on insulin secretion from rat and human islets of Langerhans. Brit. J. Pharmacol 120:926-932.

Chan et al. 1997, Evidence that the ability of imidazoline compounds to stimulate insulin secretion is not due to interaction with sigma receptors. European J Pharmacol 323:241-244.

Chan et al. 1997 Clotrimazole and efaroxan stimulate insulin secretion by different mechanisms in rat pancreatic islets. Naunyn-Scmiedeberg's Arch Pharmacol 356:763-768.

Ernsberger et al., 1997, The I1-imidazoline receptor: from binding site to therapeutic target in cardiovascular disease J. Hypertension (Supp) 15:S9-S23.

Grigg et al 1997, Isolation and partial purification of an endogenous clonidine displacing substance (CDS) from bovine brain and lung. Intl Workshop on Imidazoline receptors, Satellite Meeting to the Intl. Soc. of Autonomic Neurosciences, Melbourne Australia, Sep. 10, 1997.

Reis et al 1997 Endogenous ligands for imidazoline receptors: An update. Intl Workshop on Imidazoline receptors, Satellite Meeting to the Intl. Soc. of Autonomic Neurosciences, Melbourne Australia, Sep. 10, 1997.

Regunathan and Reis 1996, Imidazoline receptors and their endogenous ligands. Ann. Rev. Pharmacol Toxicol 36:511-44.

Atlas 1995, Molecular and physiological properties of clonidine-displacing substance. Ann N Y Acad Sci. 763:314-24.

Ernsberger et al. 1995, I1-Imadazoline receptors mediate arachidonic acid release from PC12 pheochromocytoma cells FASEB J. 9:A114.

Morgan et al. 1995, Characterization of the imidazoline binding site involved in regulation of insulin secretion. Ann. N.Y. Acad. Sci 763:361-373.

Thomas and Prell, 1995, Imidazoleacetic acid, a gamma-aminobutyric acid receptor agonist, can be formed in rat brain by oxidation of histamine. J. Neurochem. 65:818-826.

Thomas et al. 1995, Oxidation of histamine in rodent brain homogenates: evidence for an alternative pathway of brain histamine metabolism. Soc. Neurosci. Abst. 21:1857 Abstract #729.2.

Li, G et al. 1994, Agmatine: an endogenous clonidine-displacing substance in the brain. Science 263:966-968.

Thomas and Prell, 1993, Formation of 3H-Imidazoleacetic acid and its conjugates from 3H-Histamine in mammalian brain. Soc. Neurosci Abstr 19:85 Abstract #41.8.

Atlas 1991, Clonidine-displacing substance (CDS) and its putative imidazoline receptor. New leads for further divergence of alpha 2-adrenergic receptor activity. Biochemical Pharmacology 41:1541-1549.

Matulic-Adamic, 1991, Synthesis of ribosides and ribotides of Imidazole-4(5)-acetic acid and 1-Methylimidazole-4(5)-acetic acid. Korean J. Med. Chem 1:54-64.

Atlas et al. 1987, The brain's own clonidine: purification and characterization of endogenous clonidine displacing substance from brain. J Cardiovasc Pharmacol. 10 Suppl 12:S122-7.

Collins et al. 1984 German Patent Application No. DE 3446894 for New Pyrazolopyridine derivatives filed Dec. 21, 1984 (German language publication).

Collins et al 1983, UK Patent App No. GB 2121799 for "New pyrazolopyridine derivative" filed Jun. 10, 1983.

Beaven MA et al., 1976, Interference with histamine and imidazole acetic acid metabolism by salicylates: a possible contribution to salicylate analgesic activity? Experientia 32:1180-1182.

Moss J et al., 1976, Effect of salicylates on histamine and L-histidine metabolism. Inhibition of imidazoleacetate phosphoribosyl transferase. J. Clin Invest 58: 137-141.

Beaven MA et al., 1974, Inhibition by aspirin of ribose conjugation in the metabolism of histamine. Europ. J. Pharmacol. 29:138-146.

Crowley GM, 1964, The enzymatic synthesis of 5'-Phosphoribosylimidazole acetic acid. J. Biol. Chem. 239:2593-2601.

Robinson and Green, 1964, Presence of Imidazoleacetic acid riboside and ribotide in rat tissues Nature 203: 1178-1179.

Baddiley et al., 1958, Synthesis of 1—β-D-Ribofuranosy-4(5)-glyoxalinylacetic Acid, a metaboloie of Histamine J. Chem Soc. 3743-3745.

Bauer, 1958, Confirmation of the structure of imidazoleacetic acid riboside by synthesis. BBA 30:219.

Karjala SA, 1956, Urinary metabolites of radioactive histamine. J. Biol. Chem. 219:9-12.

Karjala SA, 1955, The Partial Characterization of a Histamine Metabolite From Rat and Mouse Urine J. Amer. Chem Soc 77:504-505.

Tabor and Hayaishi, 1955, The Excretion of Imidazoleacetic Acid Riboside Following the Administration of Imidazoleacetic Acid or Histamine to Rats J. American Chem. Soc. 77:505-506.

Bauer, 1962, Synthesis of 1-βD-Ribofuranosylimidazole-4(or 5)-acetonitrile, 1-β-D-Ribofuranosylimidazole-4(or 5)-acetic Acid, and 4(or 5)-(2-Aminoethyl))-1-β-D-ribofuranosylimidazole J. Org. Chem 27:167-170.

G.M. Crowley, "The Enzymatic Synthesis of 5'-Phosphoribosylimidazoleacetic Acid", The Journal Of Biological Chemistry vol. 239, No. 8, Aug. (1964).

Atlas, et al., "Isolation and partial purification of a clonidine-displacing endogenous brain substance", Eur. J. Biochem. 144, 287-293 (1984).

Atlas, et al., "Isolation of an endogenous clonidine-displacing substance from rat brain", vol. 170, No. 2 FEBS 1474 May (1984), 387-390.

Bousquet, et al., "An Endogenous, Non-Catecholamine Clonidine Antagonist Increases Mean Arterial Blood Pressure", European Journal of Pharmacology, 124 (1986) 167-170.

Dontenwill, et al., "A polyclonal antibody raised against clonidine:a model for the specific imidazoline receptor", European Journal of Pharmacology, 137 (1987) 143-144.

Dontenwill, et al., "Production and characterization of anti-clonidine antibodies not cross-reacting with catecholamines", European Journal of Pharmacology, 149 (1988) 249-255.

Belcourt, et al., "Partial purification of the human endazoline, the specific endogenous ligand for imidazoline-preferring receptors", Institut de Pharmacologie, CNRS URA 589, Faculte de Medecine, Universite Louid Pasteur, 11, rue Humann, 67000 Strasbourg, France, (1990).

Daphne Atlas, "Clonidine-Displacing Substance (CDS) And Its Putative Imidazoline Receptor", Biochemical Pharmacology. vol. 41. No. II. pp. 1541-1549. (1991).

Dotenwill, et al., "Production And Characterization Of An Iminoimidazolidine Specific Monoclonal Antibody Using Para-Aminoclonidine As Antigen", Life Sciences, (1992) vol. 50, pp. 1859-1868.

Dontenwill, et al., "A Circulating Substance Cross-reacting with Antiimidazoline Antibodies Detection in Serum in Relation to Essential Hypertension", J. Clin. Invest. vol. 92, Aug. (1993), 1068-1072.

Atlas, et al., "Identifying Clonidine-Displacing Substance", Science, vol. 266, Oct. 21, 1994, 462-463.

Singh, et al. "Evidence for the presence of a non-catecholamine, clonidine-displacing substance in crude, methanolic extracts of bovine brain and lung", Naunyn-Schmiedeberg's Arch Pharmacol (1995) 351:17-26.

Grigg, et al., "Isolation and partial structure determination of a clonidine-displacing substance from bovine lung and brain", Journal of the Autonomic Nervous System 72 (1998) 86-93.

Parker, et al., "Extraction of active clonidine-displacing substance from bovine lung and comparison with clonidine-displacing substance extracted from other tissues", European Journal of Pharmacology 378 (1999) 213-221.

Parker, et al., "Isolation of RP-HPLC pure clonidine-displacing substance from NG108-15 cells", European Journal of Pharmacology 387(2000) 27-30.

* cited by examiner

R=H, R'=PO₃H₂  IMIDAZOLEACETIC ACID-RIBOTIDE
R=R'=H  IMIDAZOLEACETIC ACID-RIBOSIDE

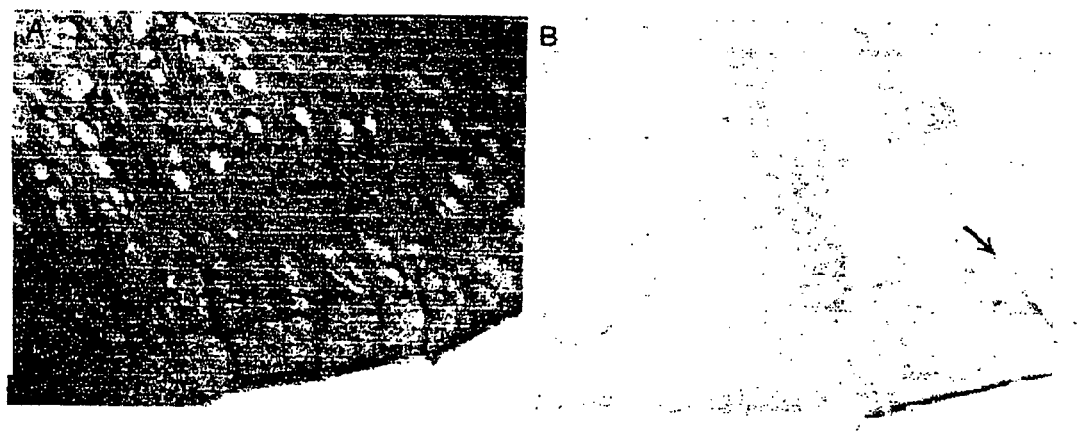
Figure 6 A-B

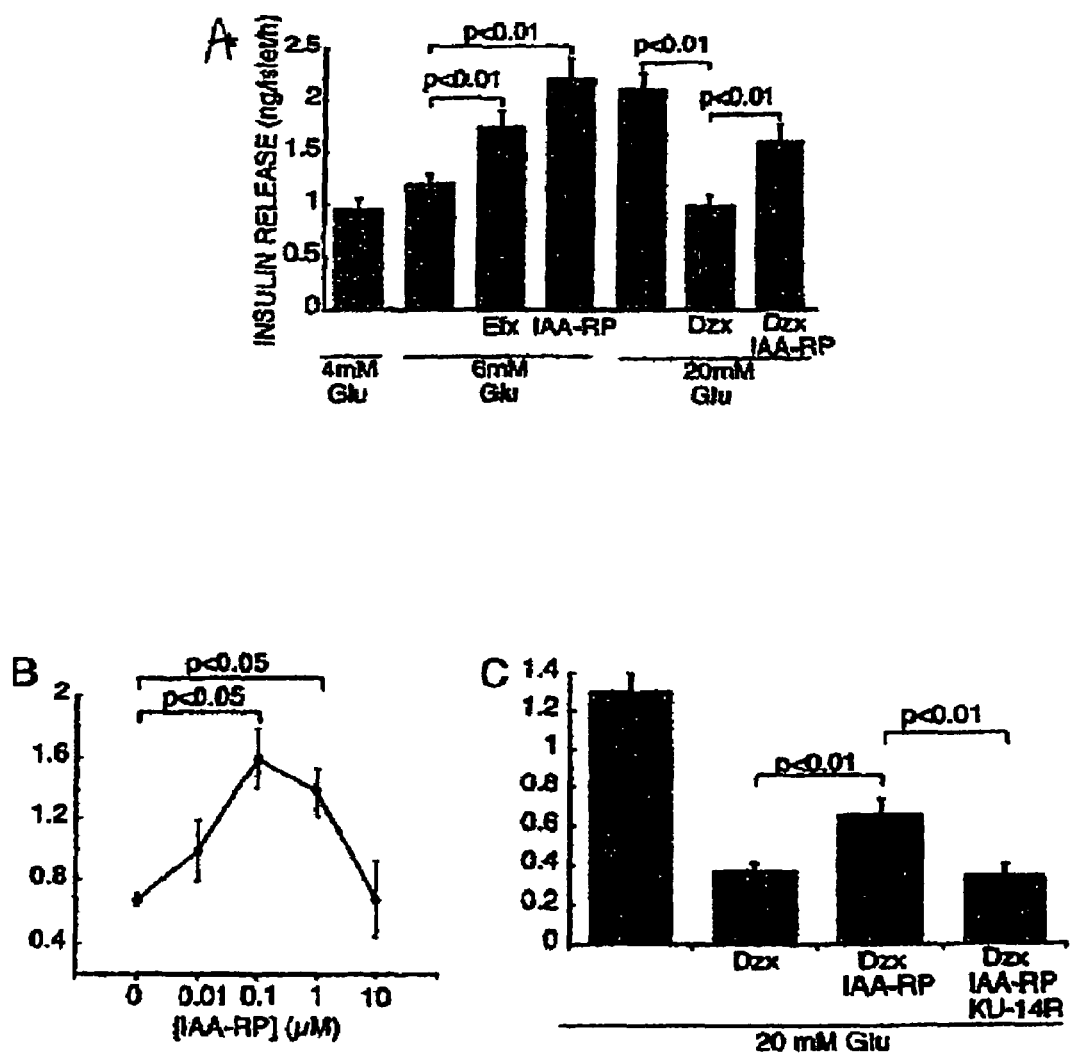
Figure 7 A-C

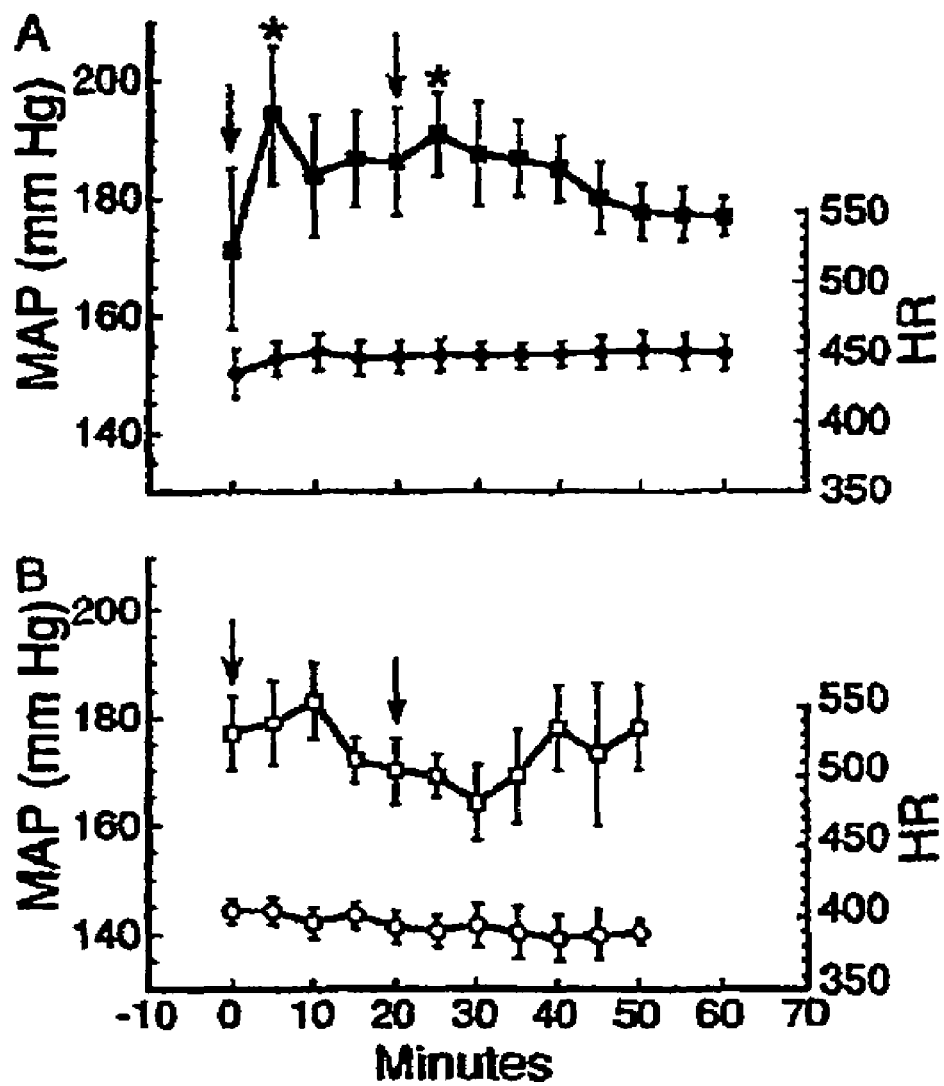
Figure 8A-B

METHODS AND COMPOSITIONS FOR REGULATING IMIDAZOLINE RECEPTORS

CROSS REFERENCE TO RELATED APPLICATIONS

This application claims priority to the following applications: the instant application is a continuation-in-part application of U.S. Pat. application Ser. No. 10/918,942 filed Aug. 16, 2004, now abandoned, which is a divisional of U.S. Pat. application Ser. No. 09/353,670, filed Jul. 15, 1999, now U.S. Pat. No. 6,777,394 issued Aug. 17, 2004, which claims priority to Provisional U.S. Application No. 60/092,945 filed Jul. 15, 1998, each of which are incorporated by reference in their entireties herein.

1. INTRODUCTION

The present invention relates to methods and compositions for regulating the activity of imidazoline receptors (also referred to as imidazol(in)e receptors). In particular, the invention relates to pharmaceutical compositions comprising imidazoleacetic acid-ribotide (IAA-RP) and imidazoleacetic acid-riboside (IAA-R). The invention is based on the discovery that IAA-RP and to a lesser extent IAA-R bind with a high affinity to imidazoline receptors. Antibodies to IAA-RP and IAA-R are additionally provided, as well as screening methods for identification of compounds that either promote or antagonize the activity of IAA-RP and IAA-R. The invention further relates to diagnostic and prognostic methods for detection of abnormalities in levels or activity of IAA-RP and IAA-R. The invention encompasses treatment of disorders related to the imidazoline system, including hypertension, glaucoma, psychiatric (e.g., depression), neurological (e.g., motor disorders, neurodegenerative disorders), diabetes and disorders related to platelet aggregation.

2. BACKGROUND OF THE INVENTION

Imidazoline receptors are now generally recognized as a unique set of non-adrenergic high affinity binding sites for a number of agents that to date also bind to $\alpha_2$-adrenergic receptors (Eglen, R. M. et al., 1998, *Trends in Pharmacol. Sci.* 19:381-390; Regunathan, S. and Reis, D. J., 1996, *Ann. Rev. Pharmacol. Toxicol.* 36:511-44). Although only one imidazoline receptors has been cloned, evidence including differences in selectivity and binding affinity of ligands, the structure of binding proteins, cellular distribution and activities indicate that they are different from $\alpha_2$-adrenergic receptors. The nonadrenergic imidazoline receptors are important in mediating the hypotensive actions of clinically important imidazoline drugs such as clonidine, rilmenidine and moxonidine.

For example, unique imidazoline receptors, are present in pancreatic islet and beta-cells (Morgan, N. G., et al., 1995, *Ann. N.Y. Acad. Sci.* 763:361-373). Activation of these receptors by imidazolines causes release of insulin. Some of this activity may be due to imidazoline-induced closure of $K^+$ channels such as the $K^+$ ATP-sensitive channels which permits intracellular levels of $K^+$ to accumulate, causing cell depolarization and eventual exocytosis of hormone or transmitter into plasma or extracellular fluid. It is noteworthy that channels such as the $K^+$ ATP-sensitive channels exist throughout the body, and are particularly abundant in brain. These pancreatic imidazoline receptors have recently been designated as $I_3$ receptor subtypes (Eglen, R. M. et al., 1998, *TIPS* 19:381-390). However, the $I_3$ subtype may not be linked to K+ ATP channels. Chan et al. (1997, *Brit. J. Pharmacol.* 120:926-932), showed that imidazolines and preparations of CDS (clonidine-displacing substance, see below) from bovine brain caused release of insulin and stimulated $K^+$ ATP channels.

One or more endogenous ligands selectively bind to the imidazoline receptors although attempts to identify this endogenous ligand(s) have failed. A possible ligand, referred to as "clonidine displacing substance" (CDS), has been discovered as an entity isolated from mammalian brain and the periphery that is capable of displacing radio-labeled clonidine and its radio-labeled congeners from membranes (Atlas, D. et al., 1987, *J. Cardiovascular Pharmacology* 10 (Suppl. 12): S122-S127; Atlas, D. 1991, *Biochemical Pharmacology* 41:1541-1549; Atlas, D., 1995, *Annals of the New York Academy of Sciences* 763:314-324). Antibodies have been prepared against the drug clonidine, which presumably interact with CDS. Such antibodies are found to be immunoreactive in tissues throughout the body and also show a heterogeneous regional distribution within the brain.

A recent study proposed that agmatine, a known compound isolated from bovine brain, is CDS (Li, G. et al., 1994, *Science* 263:966-968; Regunathan, S. and Reis, D. J., 1996, *Ann. Rev. Pharmacol. Toxicol.* 36: 511-544; but see Eglen, R. M. et al., 1998, *TIPS* 19:381-390). Agmatine was further suggested to be an endogenous neurotransmitter because it was found within an extract of CDS activity from whole brain and because it appeared to bind to a class of imidazoline receptors. However, comparisons of the biological activities of agmatine, e.g., effects on blood pressure versus effects of endogenous clonidine-displacing substance at imidazoline and $\alpha_2$-adrenergic receptors produced in virtually all laboratories, indicated that agmatine differed from "classical CDS." For example, agmatine displaces labeled clonidine from a subset of its nonadrenergic binding sites identified as imidazoline $2_A$ and $2_B$ sites. However, because those $I_{2A}$ and $I_{2B}$ sites are now known to be enzymes, i.e. portions of monoamine oxidase A and B, the search for the identity of CDS that acts at membrane-bound imidazoline receptors has continued (Eglen, R. M. et al., 1998, *TIPS* 19:381-390).

Several laboratories have harvested CDS and most preparations show similar physiochemical properties. There is widespread consensus that CDS is present in small amounts in the brain, cerebrospinal fluid and periphery (including plasma) of mammals. It is soluble in water and methanol, but generally insoluble in organic solvents. Size exclusion chromatography indicated that it is a small molecule ($\leq 1000$ Da). CDS is resistant to several proteases, including trypsin and chymotrypsin, and is devoid of amino acids; thus it is not a peptide. CDS appears to have no free amino groups as activity is retained following reaction with fluorescamine and ninhydrin. CDS is stable in both weak acids (pH 2) and weak bases (pH 10.5), is thermostable (at 110° C.) and retains activity following multiple freeze-thaw and lyophilization cycles. Because CDS can be retained on both anion and cation exchange resins and because its migration patterns shifted markedly with changes in ambient pH on gel electrophoresis, it is very likely that CDS is amphoteric, possibly a zwitterion. In addition, CDS shows maximal UV absorbance between 206-220 nm.

3. SUMMARY OF THE INVENTION

The present invention relates to methods and compositions for regulating the activity of imidazoline receptors.

Specifically, the invention relates to compositions comprising imidazoleacetic acid-ribotide (IAA-RP) which binds with high affinity to at multiple subsets of imidazoline receptors, imidazoleacetic acid-riboside (IAA-R) which binds with a slightly lower affinity, and to its related congeners. As demonstrated herein, IAA-RP binds to imidazoline receptors and in one case stimulates well defined receptor-mediated signal transduction events such as release of arachidonic acid. Further, the release of arachidonic acid, an imidazoline $I_1$-receptor mediated event, is inhibited in the presence of the imidazoline $I_1$ receptor antagonist efaroxan. Additionally, it was observed that although IAA-R binds to the imidazoline receptor, such binding failed to significantly stimulate receptor-mediated signal transduction events, thus, indicating that IAA-R may act as a partial agonist/antagonist. In anothe case, IAA-RP stimulated release of insulin from pancreatic beta cells, an $I_3$-receptor mediated event, which was blocked by the I3 antagonist KU-14R. In a paried experiment, IAA-R exhibited <50% of IAA-RP's maximal activity. Thus IAA-R acted as a partial agonist. The discovery that IAA-RP and IAA-R bind to imidazoline receptors provides new targets for therapeutic methods aimed at amelioration of imidazoline system related disorders.

The present invention includes pharmaceutical compositions comprising IAA-RP, IAA-R, derivatives and analogs thereof, which can be utilized to regulate the activity of imidazoline and imidazoline-like receptors. Such compositions can be utilized to treat disorders related to the imidazoline system such as hypertension, glaucoma, psychiatric (e.g. depression), neurological (e.g. motor disorders, neurodegenerative disorders), diabetes and disorders involving platelet aggregation.

The invention further provides for antibodies to IAA-RP and IAA-R. Such antibodies can be utilized to ameliorate symptoms associated with imidazoline system-related disorders. For example, in the case of an anti-IAA-RP antibody, such an antibody would specifically bind to IAA-RP and disrupt the ability of IAA-RP to bind to imidazoline receptors thereby preventing receptor mediated signal transduction events. Additionally, anti-IAA-RP and anti-IAA-R antibodies can be used as diagnostic and prognostic indicators of imidazoline system related disorders. For example, diagnostic methods can be utilized to detect abnormalities in the levels or tissue distribution of IAA-RP and/or IAA-R relative to normal levels. The antibodies of the invention can also be used in screening methods for detection of a predisposition to imidazoline system based disorders in an individual.

The invention further relates to methods for identification of compounds which promote or antagonize signal transduction events mediated by the binding of IAA-RP or IAA-R to imidazoline receptors. Such compounds can act as therapeutic agents in the amelioration of a wide range of imidazoline system based disorders. The invention further relates to methods for identification of compounds that regulate the synthesis, or degradation of IAA-RP or IAA-R.

Finally, the invention relates to treatment of imidazoline based disorders, such as for example, hypertension, glaucoma, psychiatric (e.g. depression), neurological (e.g. motor disorders, neurodegenerative disorders), diabetes and disorders involving platelet aggregation by administering compositions comprising IAA-RP, IAA-R, or compounds that promote or antagonize IAA-RP or IAA-R activity.

4. BRIEF DESCRIPTION OF THE DRAWINGS

FIG. 1. Chemical structures of IAA-RP and IAA-R.

Figure 2:
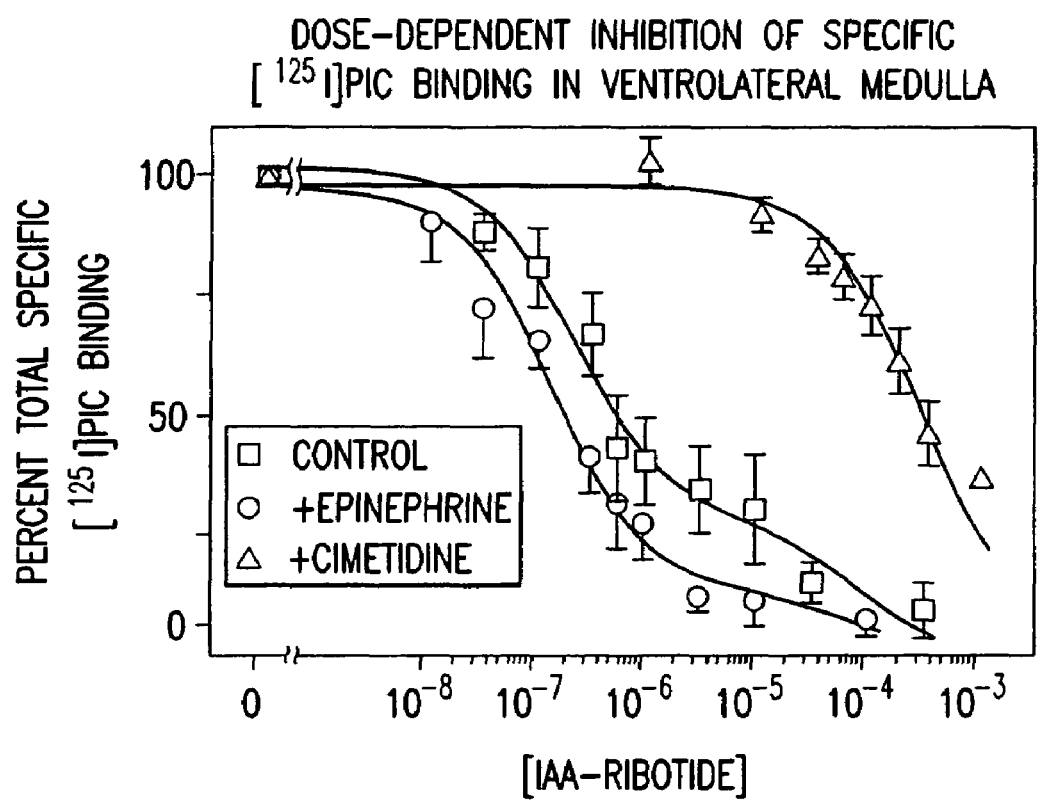

FIG. 2 Specific binding of [$^{125}$I]p-iodoclonidine (1 nM) to membrane sites in bovine RVLM. Inhibition curves were produced with increasing concentrations of IAA-RP. Total nonspecific binding was defined using BDF-6143. Curves show absence of masking ligand (▲, control), presence of epinephrine (■) to mask $\alpha_2$Rs and presence of cimetidine (♦) to mask I-Rs. Data show X±SEM of 4-6 experiments, each done in triplicate. Curves were normalized to total specific binding under each experimental condition and plotted using nonlinear curve-fitting. Each curve was normalized to the total specific binding under that condition. Results of curve-fitting analysis are shown in Table 2.

Figure 3:
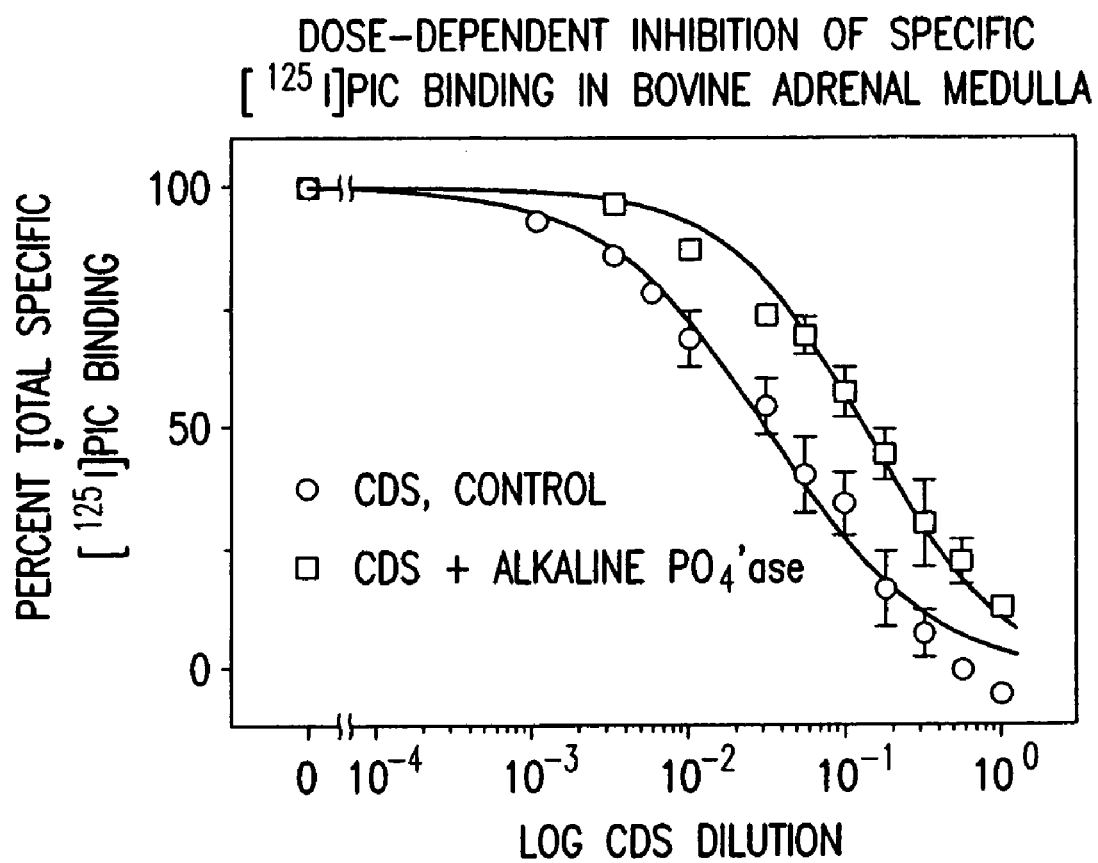

FIG. 3. Effect of phosphatase treatment on the dose-dependent inhibition of $^{125}$I-iodoclonidine binding to adrenomedullary cell membranes by brain extract containing CDS.

Figure 4:
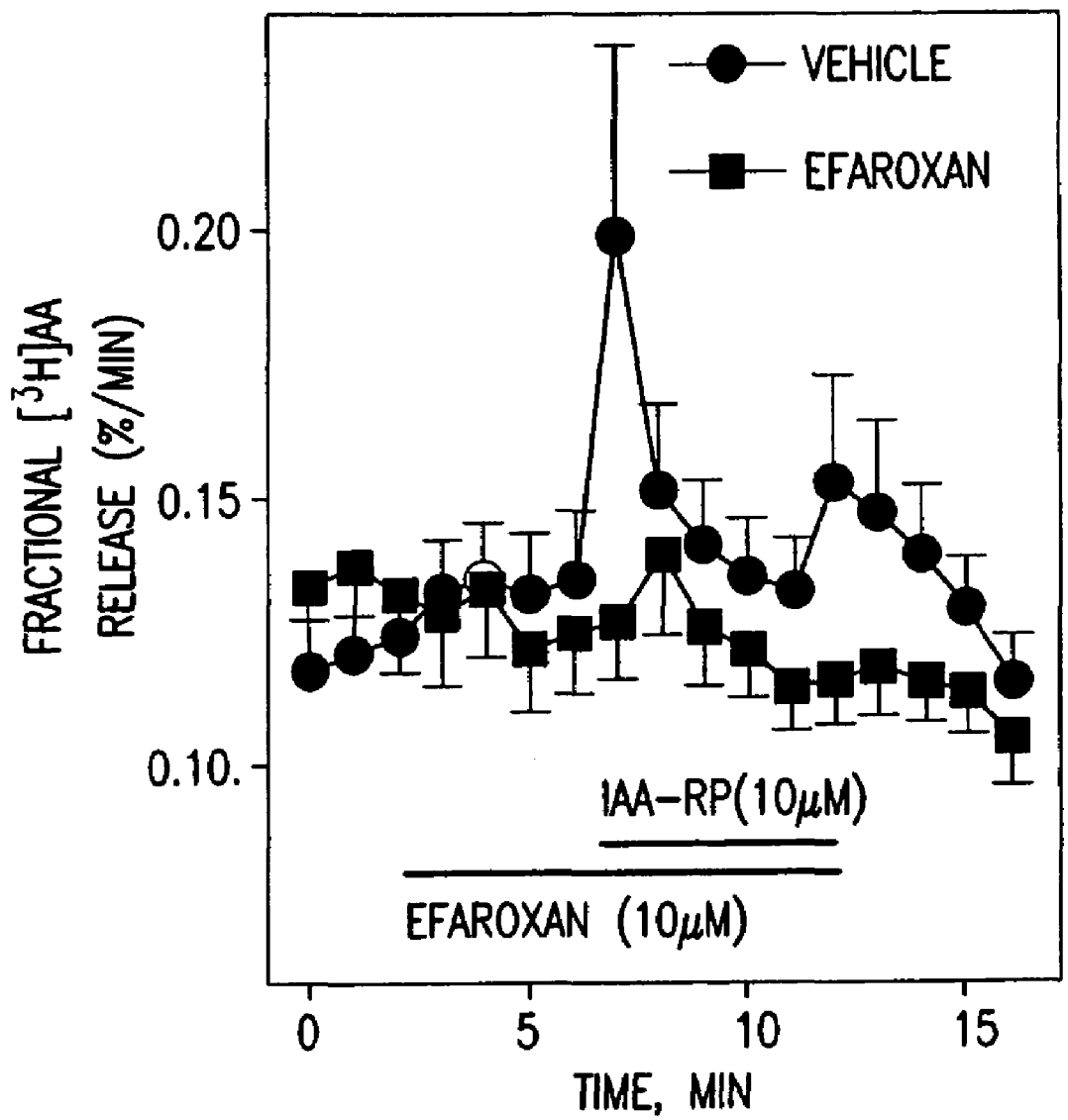

FIG. 4. IAA-RP stimulated [$^3$H]AA release from PC-12 cells. Superfusion of 10 µM IAA-RP immediately increased [$^3$H]AA release (○, X±SEM) with respect to baseline values (i.e. vehicle alone, averaged over the first 5 min) (p<0.05, Newman-Keuls; N=11). Superfusion with the $I_1$-antagonist/$I_3$-agonist efaroxan (10 µM) (□, N=11) 5 min before and throughout IAA-RP superfusion blocked IAA-RP-induced release. Before IAA-RP was added, vehicle alone or vehicle containing efaroxan exhibited stable baselines, indicating that release was due to IAA-RP's $I_1$R agonist activity.

Figure 5:
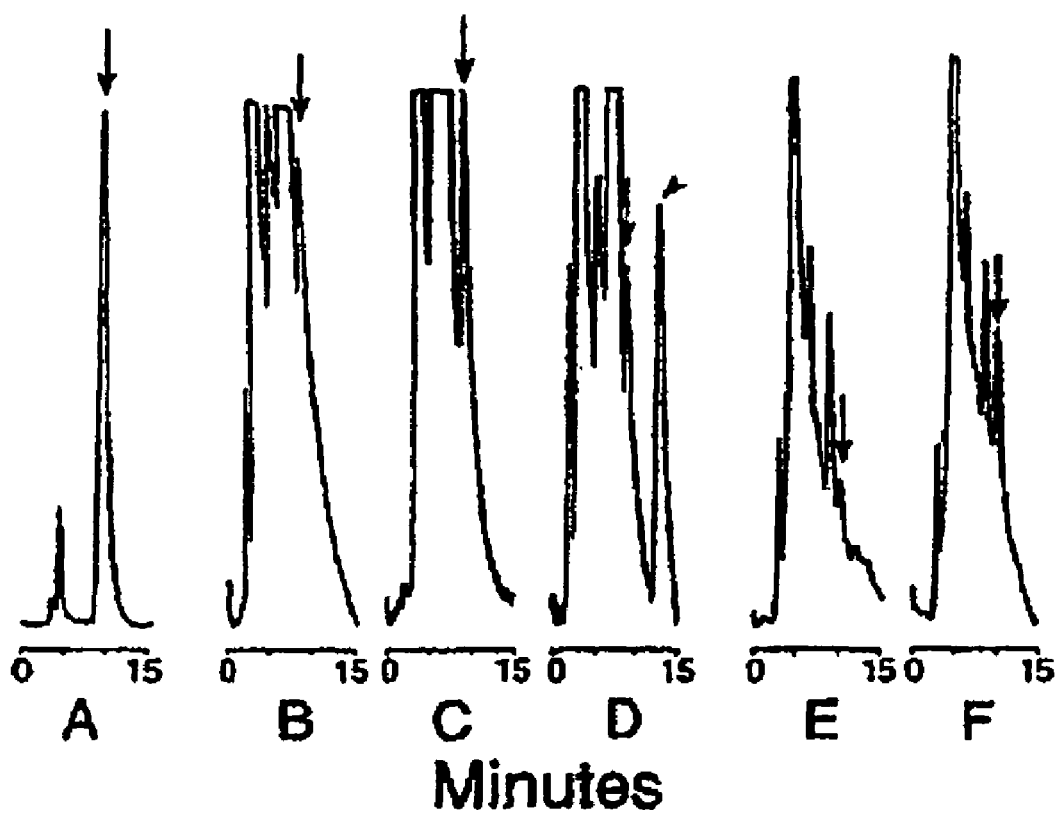

FIG. 5. Representative HPLC chromatograms showing $A_{220\,nm}$ (ordinate) after sample injections. Arrows indicate peaks corresponding to I-4-AA-RP; the arrowhead indicates the I-5-AA-RP isomer. Panels: A) authentic I-4-AA-RP [5 µg]; B) rat brain extract alone; C) parallel sample of B mixed with authentic I-4-AA-RP [183 ng]; D) parallel sample of B mixed with authentic I-5-AA-RP [200 ng]; E) sample of bovine brain extract containing CDS activity; and F) parallel sample of E mixed with authentic I-4-AA-RP [100 ng]. Signal attenuation for E and F was 0.25× that of B-D. Hereafter, the I-4-AA-RP isomer will be denoted "IAA-RP." I-4-AA-R will be denoted "IAA-R."

FIGS. 6A-B. IAA-RP immunostaining in the rat RVLM. (FIG. 6A) Anti-IAA-RP labeled neurons in the RVLM and other nuclei, showing cell bodies and the neuropil showing IAA-RP in dendritic processes. (FIG. 6B) The adjacent section, processed identically, but reacted with anti-IAA-RP Abs pre-incubated with IAA-RP (300 µM) showed no immunoreactivity. A blood vessel present in both sections is indicated with a black arrow.

FIG. 7A-C (FIG. 7A) Insulin release from rat islets in presence of glucose (Glu) alone (4, 6 and 20 mM) or combined with: i) efaroxan (Efx, 100 µM), ii) IAA-RP (1 µM), iii) diazoxide (Dzx, 200 µM), and iv) IAA-RP (1 µM) and diazoxide (200 µM) together. Each bar represents (X±SEM, N=8). Brackets denote differences (two-way ANOVA, repeated measures) between treatment groups. (FIG. 7B) Insulin release from islets incubated with increasing concentrations of IAA-RP in presence of Glu (20 mM) and diazoxide (200 µM) (N=6). (FIG. 7C) Insulin release from islets incubated in presence of Glu with: i) diazoxide (200 µM), ii) diazoxide (200 µM) and IAA-RP (1 µM), and iii) diazoxide (200 µM), IAA-RP (1 µM) and the $I_3$-blocker KU-14R (100 µM) (N=8).

FIG. 8A. IAA-RP-induced increases in mean arterial pressure (■, MAP), but not heart rate (○, HR) following microinjections (arrows) of IAA-RP (100 nmol) into the RVLM of SH rats. Symbols denote X±SEM values. Increases in MAP (p<0.01; ANOVA, repeated measures) were observed (asterisks) at 5 and 25 min (each p<0.05, Dunnett's test) when compared with rats' baseline values. FIG. 8B. Other SH rats (N=6) used as "injection controls" [MAP □; HR ○] were given vehicle containing an inert substance (see Methods). Absence of injection-related actions implies that increases in MAP were due to IAA-RP.

5. DETAILED DESCRIPTION OF THE INVENTION

The present invention relates to pharmaceutical compositions comprising imidazoleacetic acid-ribotide (IAA-RP), imidazoleacetic acid-riboside (IAA-R) and their related congeners for use in regulating the activities of imidazoline receptors. The invention is based on the discovery that IAA-RP and to a lesser extent, IAA-R have significant affinities for imidazoline receptors. Further, binding of IAA-RP to the imidazoline $I_1$ receptor in the adrenal medulla stimulates release of arachidonic acid (AA), an imidazoline $I_1$ receptor-mediated signal transduction response. The release of arachidonic acid is inhibited in the presence of efaroxan, a known antagonist of the imidazoline $I_1$ receptor. As demonstrated herein, it was also observed that although IAA-R was found to bind to the imidazoline receptors, such binding did not lead to a significant stimulation of a receptor-mediated signal transduction response indicating that IAA-R may function as a partial agonist/antagonist.

The present invention is also based on the observation that IAA-RP may participate in trans-synaptic signaling in brain, since it exists in brainstem neurons, exhibits depolarization-induced $Ca^{++}$-dependent release from $P_2$ synaptosomal elements, has relatively high affinity for membrane-bound I-R sites, and produces physiological effects upon exogenous application.

The invention encompasses compositions comprising IAA-RP, IAA-R and/or related congeners which can be utilized to regulate activities of imidazoline receptors. The invention further provides for antibodies to IAA-RP and IAA-R. Such antibodies can be utilized to ameliorate imidazoline related disorders. Alternatively, anti-IAA-RP and anti-IAA-R antibodies can be used diagnostically and prognostically to detect abnormalities in levels or tissue distribution of IAA-RP and/or IAA-R relative to normal levels.

The discovery that IAA-RP, IAA-R and related congeners bind to imidazoline receptors provides a new target for therapeutic methods aimed at amelioration of imidazoline system related disorders. Thus, the invention further relates to methods for identification of compounds which promote or antagonize the biological activity stimulated by IAA-RP, IAA-R and related congeners that bind to imidazoline receptors. Such compounds can act as therapeutic agents in the amelioration of a wide range of imidazoline based disorders.

Finally, the invention relates to treatment of imidazoline system based disorders, such as hypertension, glaucoma, psychiatric (e.g. depression), neurological (e.g. motor disorders, neurodegenerative disorders), diabetes and disorders involving platelet aggregation by administering compositions comprising IAA-RP, IAA-R, related congeners, and/or compounds that promote or antagonize IAA-RP or IAA-R activity.

5.1. Pharmaceutical Compositions Containing IAA-RP, IAA-RP and their Related Congeners The present invention provides pharmaceutical compositions containing imidazoleacetic acid ribotide (IAA-RP) or imidazoleacetic acid riboside (IAA-R). FIG. 1 depicts the tele-linked isomers of IAA-RP and IAA-R. IAA-RP, or tele-linked IAA-RP, is also known as imidazole-4-acetic acid-ribotide as well as 1-(β-D-ribofuranosyl)-imidazole-4-acetic acid 5' phosphate. Its metabolite, IAA-R or tele-linked IAA-R, is also known as imidazole-4-acetic acid-riboside or as 1-(β-D-ribofuranosyl)-imidazole-4-acetic acid. Both compounds exhibit covalent imidazole-furan linkage with the imidazole nitrogen atom furthest from the methylene-carboxy side chain. This atom is termed the tele-N or $N^\tau$, analogous to the IUPAC terms used to define the nitrogen atoms of histidine. The corresponding pros-linked isomers of IAA-RP and IAA-R, are termed 1-(β-D-ribofuranosyl)-imidazole-5-acetic acid 5' phosphate or pros-linked IAA-RP and 1-(β-D-ribofuranosyl)-imidazole-5-acetic acid or pros-linked IAA-R, respectively. For these compounds, the imidazole-furan linkage is with the pros-N or $N^\pi$, i.e., the imidazole ring nitrogen closest to the methylene-carboxy side chain.

In addition, pharmaceutical compositions comprising congeners and derivatives of IAA-RP and IAA-R which have a high affinity for imidazoline receptors are within the scope of the present invention. As referred to herein, congeners are defined as chemical compounds closely related to another in structure and exerting similar or antagonistic effects. For example, structural isomers of IAA-RP with, for example, the addition of one or more phosphate or phosphonate groups, i.e, IAA-RPP, IAA-RPPP, IAA-RPPP, IAA_RcP, IAA-RPPcP, etc., are included in the scope of the present invention.

In general, the invention comprises ribosylated imidazoles, such as imidazole-furanosyl ribotides and ribosides, including but not limited to compounds such as 5-amino-4-imidazole carboxamide-ribosephosphate (AICARP, also commonly abbreviated ZMP), an intermediate in the de novo synthesis pathway of purine nucleotides. In addition, substitution of a methylene group ($—CH_2—$) for the oxygen atom that links the 5' carbon to the phosphate atom in IAA-RP, can be done to produce a molecule that is much more resistant to enzymatic dephosphorylation by phosphatases or 5' nucleases. Such molecules would have more desirable pharmacokinetic properties. In addition, 2' or 3' deoxy-IAA-RP which retain affinity for the imidazoline receptor are within the scope of the present invention. Compounds within the scope of the invention also include esters of IAA-RP, such as carboxy-methyl or carboxy-ethyl esters of IAA-RP. Such compounds are more lipid soluble, and thus, would diffuse more rapidly across biological barriers such as the blood-brain barrier or cells lining the gut.

Additionally, molecules within the scope of the invention include those compounds with linkage of the furan to the number 2 carbon atom of the imidazole ring, i.e, the carbon atom in between the two imidazole ring nitrogens. Alternatively, the furan ring may be linked to the number 2 carbon atom of the imidazole ring, with reduction of the double bond between carbons 4 and 5, leading to the conversion of the imidazole ring to an imidazoline ring or an imidazoline-like ring. Molecules within the scope of the invention also include those whose imidazole or imidazoline ring nitrogen atoms are substituted with other heteroatoms, for example, substitution of either or both nitrogen atoms for oxygen or sulfur.

Methods for synthesis of IAA-RP and IAA-R are well known to those of skill in the art and include both biosynthetic and organic methods of synthesis. Methods for recovery and purification of IAA-RP and IAA-R from biological samples are described in various references (Karjala, S. A., 1955, *J. Amer. Chem. Soc.* 77:504-505; Tabor, H. and Hayaishi, O., 1955, *J. Amer. Chem. Soc.* 77:505-506: Crowley, G. M., 1964, *J. Biol. Chem.* 239: 2593-2601; Karjala, S. A. et al., 1956, *J. Biol. Chem.* 219:9-12; Beaven, M. A. et al., 1974, *Europ. J. Pharmacol.* 29:138-146; Moss, J. et al., 1976, *J. Clin. Invest.* 58:137-141; Robinson, J. D. and Green, J. P., 1964, *Nature* 203:1178-1179; Beaven, M. A. et al., 1976, *Experientia* 32:1180-1182; Thomas, B. and Prell, G. D., 1993, *Soc. Neurosci. Abst.* 19:85; Thomas, B. and Prell, G. D., 1995, *J. Neurochem.* 65: 818-826; Thomas, B. et al., 1995, *Soc. Neurosci. Abst.* 21:1857).

In addition, organic synthesis of IAA-R can be carried out using the method of Bauer (1958, BBA 30:219; and 1962, *J. Org. Chem.* 27:167-170; Baddiley, J. et al, 1958, *J. Chem. Soc.* 3743-3745). The 5' hydroxyl group on IAA-R can be phosphorylated as presented in Matulic'-Adamic', J. and Watanabe, K. A. (1991, *Korean J. Med. Chem.* 1:54-64) to yield IAA-RP. In addition, IAA-RP can be enzymatically synthesized from IAA-R using for example, enzymes such as adenosine kinase (ATP:adenosine 5' phosphotransferase) to transfer a terminal phosphate from ATP to IAA-R, to produce IAA-RP. The resultant IAA-RP can be rapidly purified using any of a variety of methods including anion exchange, HPLC and TLC. Some other congeners of tele-linked IAA-RP and IAA-R (including synthesis of pros-linked IAA-RP and IAA-R) (FIG. 1) are described elsewhere (e.g. Matulic'-Adamic', J. and Watanabe, K. A., 1991,*Korean J. Med. Chem.* 1:54-64).

In some instances it may be advantageous to transfer a labeled terminal phosphate from ATP to IAA-R to produce labeled IAA-RP, i.e., IAA-R$^{32}$ P. Such labeled IAA-RP will have a number of different uses including use in binding and receptor studies, during screens developed for identification of compounds having an affinity for imidazoline receptors, for isolation of imidazoline receptors as well as for analysis of the binding domains of imidazoline receptors. In addition, labeled IAA-RP can be used in pulse-chase studies of IAA-RP metabolism, analysis of IAA-RP's pharmacokinetic properties, and analysis of IAA-RP recovery in analytical methods.

To determine whether the tele- or pros-form of IAA-RP and IAA-R is present in the brain, pulse-chase experiments involving the administration of radiolabeled precursor produce IAA-RP and IAA-R were done. Using an anion-exchange HPLC/UV method we were able to separate imidazole-4-acetic acid-ribotide from imidazole-5-acetic acid-ribotide; it was determined that IAA-RP is present in rat brain, human brain, cerebrospinal fluid and preparations of CDS harvested from bovine brains. Only imidazole-4-acetic acid-ribotide, i.e., the isomer in which the furan ring is linked to the imidazole tele-nitrogen (the nitrogen located furthest from the CH$_2$COOH side chain; see, FIG. 1) was consistently observed. Furthermore, HPLC analysis of biological samples mixed with authentic tele-linked IAA-RP prepared by organic synthesis, produced a larger UV absorption peak coincident with the tele-linked IAA-RP retention time. No split peaks or additional peaks were observed in this region of the HPLC chromatogram.

In contrast, mixing parallel biological aliquots with authentic imidazole-5-acetic acid-ribotide, i.e., the isomer in which the furan ring is linked to the pros or π ring nitrogen (the imidazole ring nitrogen located closest to the —CH$_2$COOH side chain) produced a novel nonphysiological peak where previously there had been essentially baseline absorbance. This new peak was approximately 2-3 minutes behind the endogenous IAA-RP peak, a shift in retention virtually identical to that observed for I-5-AA-RP when authentic I-4-AA-RP and I-5-AA-RP were analyzed alone or together. Thus, there appears to be little or no I-5-AA-RP in the biological material we analyzed. These observations are consistent with observations made using gas chromatography-mass spectrometry where the tele-linked IAA-riboside, but not pros-linked IAA-riboside, was present in biological samples including rat brain. In addition, the tele-linked isomer of IAA-RP shows significant activity for displacing clonidine from its nonadrenergic membrane binding sites in the adrenal medulla.

The fact that pros-linked IAA-RP or pros-linked IAA-R does not seem to be present in samples of rat brain nevertheless suggest a number of uses of pros-linked IAA-RP. For example, pros-linked IAA-RP, or pros-linked IAA-R, can be used as an internal standard in analytical techniques such as for example, in HPLC methods, to determine recovery of endogenous tele-linked IAA-RP. The pros-linked IAA-RP can also be used as a control substance when the activities of the endogenous tele-linked IAA-RP are to be assessed. More importantly, they can interact with imidazoline receptors. In cases such as with imidazoline I$_3$ or I$_3$-like receptors, pros-linked IAA-R has its own activities on insulin release and may also interact with K+ ATP channels.

The pharmaceutical compositions of the invention comprise an effective amount of IAA-RP, IAA-R, and related congeners and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such pharmaceutical compositions will contain a therapeutically effective amount of IAA-RP, IAA-R, and/or a related congener, preferably in purified form, together with a suitable amount of carrier so as to provide the form for proper administration to the patient. The formulation should suit the mode of administration.

5.2. Generation of Antibodies to IAA-RP, IAA-R or Related Congeners

According to the invention, IAA-RP, IAA-R or related congeners may be used as immunogens to generate antibodies which immunospecifically bind such immunogens. Such antibodies include, but are not limited to polyclonal, monoclonal, chimeric, single chain, Fab fragments, and Fab expression library.

Various procedures known in the art may be used for the production of polyclonal antibodies to IAA-RP or IAA-R or derivatives or analogs thereof. In a particular embodiment, rabbit polyclonal antibodies to an epitope of IAA-RP or IAA-R can be obtained. For the production of antibody, various host animals can be immunized by injection with IAA-RP or IAA-R, or a synthetic version, or derivative thereof, including but not limited to rabbits, mice, rats, etc. Various adjuvants may be used to increase the immunological response, depending on the host species, and including, but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

In a specific working example described herein, polyclonal antibodies reactive against IAA-RP were successfully generated in rabbits immunized with I-4-AA-RP linked to keyhole limpet hemocyanin. Such polyclonal antibodies have been successfully utilized in immunochemical studies designed to study the biological properties associated with IAA-R activity.

For preparation of monoclonal antibodies directed toward IAA-RP or IAA-R or analogs thereof, any technique which provides for the production of antibody molecules by continuous cell lines in culture may be used. For example, the hybridoma technique originally developed by Kohler and Milstein (1975, *Nature* 256:495-497), as well as the trioma technique, the human B-cell hybridoma technique (Kozbor et al., 1983, *Immunology Today* 4:72), and the EBV-hybridoma technique to produce human monoclonal antibodies (Cole et al., 1985, in *Monoclonal Antibodies and Cancer Therapy*, Alan R. Liss, Inc., pp. 77-96). According to the invention, human antibodies may be used and can be obtained by using human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, pp. 77-96). In fact, according to the invention, techniques developed for the production of "chimeric antibodies" (Morrison et al., 1984, *Proc. Natl. Acad. Sci.* U.S.A. 81:6851-6855; Neuberger et al., 1984, *Nature* 312:604-608; Takeda et al., 1985, *Nature* 314:452-454) can be used; such antibodies are within the scope of this invention.

In the production of antibodies, screening for the desired antibody can be accomplished by techniques known in the art, e.g., ELISA (enzyme-linked immunosorbent assay). Various immunoassays known in the art can be used to determine the binding characteristics of the antibodies, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), IAA-RP or IAA-R precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

The foregoing antibodies can be used in methods known in the art relating to the localization and activity, e.g., for imaging IAA-RP and IAA-R molecules, measuring levels thereof in appropriate physiological samples, in diagnostic methods, etc. In another embodiment of the invention, anti-IAA-RP or anti-IAA-R antibodies and fragments thereof containing the binding domain can be used to regulate the activity of imidazoline receptors.

5.3. Diagnosis and Screening

Anti-IAA-RP and -IAA-R antibodies, have uses in diagnostics. Such molecules can be used in assays, such as immunoassays, to detect, prognose, diagnose, or monitor various conditions, diseases, and disorders affecting the imidazoline system. In particular, such an immunoassay is carried out by a method comprising contacting a sample derived from a patient with an anti-IAA-RP or anti-IAA-R antibody under conditions such that immunospecific binding can occur, and detecting or measuring the amount of any immunospecific binding by the antibody. In a specific aspect, such binding of antibody, in samples derived from the patient, can be used to detect aberrant IAA-RP or IAA-R localization or aberrant (e.g., high, low or absent) levels of IAA-RP or IAA-R. In a specific embodiment, antibody to IAA-RP or IAA-R can be used to assay in a patient tissue or serum sample for the presence of IAA-RP or IAA-R where an aberrant level of IAA-RP or IAA-R is an indication of a diseased condition. By "aberrant levels," is meant increased or decreased levels relative to that present, or a standard level representing that present, in an analogous sample from a portion of the body or from a subject not having the disorder.

The immunoassays which can be used, include but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, to name but a few.

Kits for diagnostic use are also provided that comprise in one or more containers an anti-IAA-RP or IAA-R antibody, and, optionally, a labeled binding partner to the antibody. Alternatively, the anti-IAA-RP or IAA-R antibody can be labeled (with a detectable marker, e.g., a chemiluminescent, enzymatic, fluorescent, or radioactive moiety). Additionally, Anti-IAA-RP antibiodies can also be utililized to study the biological properties of IAA-RP.

5.4. Screening for Agonists and Antagonists of IAA-RP, IAA-R and Related Congeners A variety of different assay systems can be designed and used to identify compounds or compositions that modulate IAA-RP or IAA-R activity, and therefore, may be useful to regulate imidazoline receptors and useful in the treatment of diseases associated with the imidazoline system.

In accordance with the invention, cell-based assay systems are used to screen for compounds that modulate the activity of IAA-RP and IAA-R and thereby modulate the activity of imidazoline receptors. Compounds that may affect IAA-RP and/or IAA-R activity include, but are not limited to compounds that promote (agonists) or block (antagonists) activation of imidazoline receptors.

To this end, cells that endogenously express imidazoline receptors can be used to screen for compounds that modulate IAA-RP activity. Cells that express imidazoline receptors can be further engineered to incorporate a reporter molecule, the expression of which is linked to the signal transduced by IAA-RP or related congener activation of imidazoline receptors to aid in identification of compounds that modulate activity. Cells to be used to screen for compounds are cells that respond to activation of imidazoline receptors by IAA-RP, or their congeners, e.g., as measured by a chemical, physiological, biological, or phenotypic change. For example, a test compound may be used to assess the ability for IAA-RP or a related congener to bind to imidazoline receptors and thereby inhibit or activate signal transduction processes. In one case, release of arachidonic acid can be used to assess imidazoline $I_1$ activity. In addition, release of insulin and/or closure of $K^+$ ATP channels can be used to assess imidazoline $I_3$ activity.

In utilizing such cell-based assay systems, cells that express imidazoline receptors are exposed to a test compound or to vehicle controls (e.g., placebos). After exposure, the cells can be assayed to measure the expression and/or activity of components of the signal transduction pathway affected by IAA-RP, IAA-R or their congeners. For example, in cells of the adrenal medulla that express imidazoline $I_1$ receptors, binding of IAA-RP and IAA-R are associated with release of arachidonic acid; thus, in a specific embodiment of the invention, assays may be designed to measure arachidonic acid. The ability of a test compound to decrease levels of arachidonic acid release, as compared to those levels seen with cells treated with a vehicle control, indicates that the test compound inhibits signal transduction mediated by binding of IAA-RP, IAA-R or a related congener to an imidazoline $I_1$ receptor. In addition, assays may be developed to measure IAA-RP or IAA-R induced release of insulin from pancreatic β-cells or release of catecholamines from chromaffin cells.

Non-cell based assays may be used to identify compounds that bind to IAA-RP or IAA-R molecules. The principle of assays used to identify compounds that bind to IAA-RP or IAA-R involves preparing a reaction mixture of the molecules and the test compound under conditions and for time sufficient to allow the two components to interact and bind, thus forming a complex which can be removed and/or detected in the reaction mixture. The identity of the bound test compound is then determined.

The screening assays are accomplished by any of a variety of commonly known methods. For example, one method to conduct such an assay involves anchoring the IAA-RP, IAA-R, or a related congener onto a solid phase and detecting IAA-RP or IAA-R/test compound complexes retained on the solid phase at the end of the reaction. In one embodiment of such a method, the IAA-RP or IAA-R reactant is anchored onto a solid surface, and the test compound, which is not anchored, may be labeled, either directly or indirectly.

In practice, microtitre plates can be utilized conveniently as the solid phase. The anchored component is immobilized by non-covalent or covalent attachments. The surfaces may be prepared in advance and stored. In order to conduct the assay, the non-immobilized component is added to the coated surfaces containing the anchored component. After the reaction is completed, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the solid surface; e.g., using a labeled antibody specific for the previously non-immobilized component.

Alternatively, a reaction is conducted in a liquid phase, the reaction products separated from unreacted components using an immobilized antibody specific for IAA-RP, IAA-R, or a related congener, fusion protein or the test compound, and complexes detected using a labeled antibody specific for the other component of the possible complex to detect anchored complexes.

Assay for compounds that interfere with the interaction of IAA-RP, IAA-R, or related congeners with imidazoline receptors can be performed. Ligand/receptor interactions can be detected at the end of the reaction comparing interactions in the presence or absence of test compound. The order of addition of test compounds can be varied to obtain different information about the compounds being tested. For example, test compounds that interfere with the interaction by competition can be identified by conducting the reaction in the presence of the test compound, i.e., by adding the test compounds to the reaction mixture prior to or simultaneously with IAA-RP, IAA-R, or a related congener. Alternatively, test compounds that disrupt preformed complexes, i.e, those compounds with higher binding constants that displace one of the components from the complex, can be tested by adding the test compound to the reaction after the complexes have formed.

In addition, assays may be used to identify compounds that interfere with the expression or degradation of IAA-RP or IAA-R. For example, IAA-RP is synthesized by imidazoleacetic acid phosphoribosyltransferase (IPRT) (Thomas, B. and Prell, G. D., 1995, *J. Neurochem*. 65:818-826). In an embodiment of the present invention, assays may be developed to identify compounds which inhibit IPRT thereby reducing levels of IAA-RP and/or IAA-R. Alternatively, such assays may be used to identify compounds that activate IPRT resulting in elevated levels of IAA-RP and/or IAA-R. In a non-limiting embodiment of the invention, antibodies directed against IAA-RP or IAA-R may be used in the assays of the invention to detect changes in levels of IAA-RP and/or IAA-R.

IAA-RP is metabolized to IAA-R by dephosphorylation through the action of either 5' phosphatases and/or 5' nucleotidases (endo or ecto). Inhibition of such phosphatases or nucleotidases would result in accumulation of IAA-RP and/or reductions in levels of IAA-RP. Alternatively, activation of such phosphatases and/or nucleotidases would result in reduction in levels of IAA-RP and/or an increase in levels of IAA-R. In yet another embodiment of the invention, assays may be developed to identify compounds capable of regulating the activity of 5' phosphatases and/or 5' nucleotidases.

Based on experiments described herein, it is believed that IAA-RP is released as a neurotransmitter, where it can be metabolized at the cell surface by phosphates and nucleotidases to form IAA-R. IAA-R is then transported into the cell and resynthesized into IAA-RP in a general transmitter cycling mechanism. Alternatively, IAA-RP may be taken up directly from the synapse by a transporter process. Thus, in yet another embodiment of the invention, assays may be developed to identify compounds capable of regulating the cycling mechanism leading to formation of IAA-RP and IAA-R. For example, screens may be designed to identify compounds which block IAA-R uptake leading to accumulation of IAA-R in the synapse. Accumulation of IAA-R within the synapse might lead to reduction of IAA-RP mediated activity through, for example, accumulation of less active IAA-A to act as a partial agonist/antagonist or reduction in amounts of IAA-RP to be produced through the cycling mechanism. Such compounds may be used to treat disorders mediated by the activity of IAA-RP and IAA-R.

The compounds which may be screened in accordance with the invention include, but are not limited to inorganic compounds, peptides, antibodies and fragments thereof, and other organic compounds (e.g., peptidomimetics) that bind to imidazoline receptors and either mimic the activity of IAA-RP, IAA-R or a related congener (i.e., agonists) or inhibit the activity of IAA-RP, IAA-R (i.e., antagonists). Compounds may include, but are not limited to, peptides such as, for example, soluble peptides, including but not limited to members of random peptide libraries; (see, e.g., Lam, K. S. et al., 1991, *Nature* 354:82-84; Houghten, R. et al., 1991, *Nature* 354:84-86), and combinatorial chemistry-derived molecular library made of D- and/or L-configuration amino acids, phosphopeptides (including, but not limited to, members of random or partially degenerate directed phosphopeptide libraries; see, e.g., Songyang, Z. et. al., 1993, *Cell* 72:767-778).

5.5. Treatment and Prevention of Disorders Involving the Imidazoline System

Diseases and disorders involving imidazoline receptors are treated or prevented by administration of a compound that either promotes or antagonizes the activity stimulated by binding of IAA-RP, IAA-R or a related congener to imidazoline receptors.

In specific embodiments, compositions that promote IAA-RP or IAA-R function are administered to an individual: (1) in diseases or disorders involving an absence or decreased (relative to normal or desired) level of IAA-RP or IAA-R, for example, in patients where the IAA-RP or IAA-R are lacking, biologically inactive or underactive, or under expressed; or (2) in diseases or disorders wherein in vitro (or in vivo) assays indicate that the utility of IAA-RP, IAA-R or a related congener agonist administration. The absence or decreased level of IAA-RP or IAA-R can be readily detected, e.g., by obtaining a patient tissue sample (e.g., from biopsy tissue) and assaying levels. Many methods standard in the art can be thus employed, including but not limited to assays for biological activity (e.g. arachidonic acid, insulin, and catecholamines release), immunoassays to detect and/or visualize IAA-RP or IAA-R (e.g., Western blot, immunoprecipitation followed by sodium dodecyl sulfate polyacrylamide gel electrophoresis, immunocytochemistry, ELISA assays, etc.).

In some instances, imidazoline system-based disorders can be treated or prevented by administration of a composition that antagonizes (inhibits) IAA-RP or IAA-R function. Compounds that inhibit IAA-RP or IAA-R function can be identified by use of known convenient in vitro assays, e.g., based on their ability to inhibit binding of IAA-RP or IAA-R to imidazoline receptors. Preferably, suitable in vitro or in vivo assays are utilized to determine the effect of a specific compound and whether its administration is indicated for treatment of the affected tissue.

In specific embodiments, compounds that inhibit IAA-RP or IAA-R function are administered therapeutically (including prophylactically): (1) in diseases or disorders involving an increased (relative to normal or desired) level of IAA-RP or IAA-R; or (2) in diseases or disorders wherein in vitro (or in vivo) assays indicate the utility of IAA-RP or IAA-R antagonist administration. The increased levels in IAA-RP or IAA-R concentration and/or function can be readily detected, e.g., by quantifying levels, by obtaining a patient tissue sample (e.g., from biopsy tissue) and assaying it in vitro for levels of the molecules, and/or activity of the molecules. Many methods standard in the art can be thus employed, including but not limited to assays for detecting release of arachidonic acid (e.g. in the case of disorders affected by imidazoine $I_1$ receptors), immunoassays to detect and/or visualize IAA-RP or IAA-R (e.g., immunocytochemistry, in situ hybridization, ELISA assays, etc.).

The compositions of the invention are preferably tested in vitro, and then in vivo for the desired therapeutic or prophylactic activity, prior to use in humans. For example, in vitro assays can be used to determine whether administration of a specific compound is indicated, including in vitro cell culture assays in which a patient's tissue sample is grown in culture and exposed to the compound, and the effect of such compound upon the tissue sample is observed. For example, compositions can be tested for their ability to either stimulate or inhibit the binding of IAA-RP, IAA-R or related congeners to imidazoline receptors. Alternatively, the ability of a compound to inhibit or stimulate receptor mediated signal transduction events, such as release of arachinoic acid (in the case of $I_1$ receptors) can be tested.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

5.6. Administration of Pharmaceutical Compositions

Various delivery systems are known and can be used to administer the compositions of the invention, e.g. encapsulation in liposomes, microparticles, microcapsules. Methods of introduction include, but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

The amount of the compositions of the invention which may be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLE

IAA-RP and IAA-R Bind to the Imidazoline Receptor

In the example detailed below, binding of IAA-RP, IAA-R and related congeners to imidazoline receptors was demonstrated. In addition, IAA-RP induced the release of arachidonic acid, an imidazoline $I_1$ receptor mediated response in cultured medullary adrenal cells and the $I_1$ receptor antagonist efaroxan was found to inhibit this IAA-RP-induced release of arachidonic acid.

6.1. Materials and Methods

6.1.1 Tissue Preparation

Whole bovine brains and adrenal glands were obtained from a local slaughterhouse. Brains were immediately placed on a chilled glass plate, washed with ice-cold Krebs'-Henseleit buffer, and dissected. The rostral medulla was isolated by transecting the brainstem rostrally at the posterior margin of the trapezoid body and caudally 1 cm caudal to the obex. The pia-arachnoid was removed, and the lateral medulla was isolated by a sagittal section through the lateral margin of the pyramids, and then bisected. The ventral half was defined as the ventrolateral medulla (VLM). Brain samples were transported on ice to the laboratory and processed immediately.

Fresh bovine adrenal glands (<10 min post-mortem) were dissected free of associated fat and connective tissue and perfused retrogradely through the adrenal vein with 25 ml ice-cold Krebs'-Henseleit bicarbonate buffer. The glands were drained and reperfused with Krebs'-Henseleit buffer, drained, and then perfused again with 25 ml ice-cold Krebs'-Henseleit buffer containing 0.025% collagenase (type D, Boehinger Mannheim). The glands were incubated with occasional mixing during transport to the laboratory (about one hour), then perfused with 25 ml fresh buffer containing collagenase and incubated for 30 min at 35° C. The digested glands were split and the medulla was scraped away from the cortex and placed under 20 ml of buffer containing collagenase. Adrenal medullae were mechanically minced (Tekmar Tissuemincer, setting 40 for 30 sec) and incubated with stirring for 30 min at 37° C. The digest was filtered through stainless steel mesh and the filtrate centrifuged at 200×g for 10 min at 20° C. The cell pellet was resuspended in 30 ml Krebs' without collagenase, recentrifuged, lysed by flash-freezing, and stored overnight at −70° C. About 70% of the cells isolated in this way are chromaffin cells as shown by neutral red staining.

6.1.2 Membrane Preparation

Fresh bovine VLM was homogenized by using a polytron (Tekmar Tissuemizer, setting 80 for 2×15 sec) in 20 volumes of ice-cold Hepes-buffered isotonic sucrose (pH brought to 7.4 with Tris base) containing the protease inhibitors (1,10)-phenanthroline (100 μM) and phenylmethylsulfonyl fluoride (50 μM) in order to inhibit degradation of receptor protein. Bovine adrenomedullary cells were homogenized in 15 ml Hepes-buffered isotonic sucrose by 10 strokes in a glass-glass hand-held homogenizer. All three homogenates were centrifuged at 1000×g for 5 min at 4° C. to remove nuclei and debris. The pellets (P1) were resuspended in 20 ml of homogenization buffer, and centrifuged again at 1000×g for 5 min. The combined supernatants were centrifuged at 48,000 g for 18 min at 4° C., and the resulting P2 pellet was resuspended in 10 to 25 volumes of 50 mM Tris-HCl buffer (pH 7.7) containing 5 mM EDTA. After recentrifugation at 48,000 g for 18 min, the resulting membrane pellet was resuspended in Tris-HCl containing 25 mM NaCl, preincubated for 30 min at 25° C., chilled on ice, centrifuged again, resuspended a final time in Tris-HCl alone, centrifuged, flash-frozen, and stored at −70° C. for up to three months.

6.1.3 [$^3$H]Clonidine AND [$^{125}$I]p-Iodoclonidine Binding Assays

Radioligand binding assays with [$^3$H]clonidine or [$^{125}$I] p-iodoclonidine for determination of specific membrane binding to VLM and renal medulla imidazoline sites and $\alpha_2$-adrenergic receptors were performed by a modification of methods previously described (Ernsberger P. et al., 1997, *J. Hypertension* 1997, 15:S9-S23). Membranes were slowly thawed and resuspended in Tris-Hepes buffer (5.0 mM; pH 7.7 at 25° C., containing 0.5 mM EDTA, 0.5 mM EGTA, and 0.5 mM MgCl$_2$) at a concentration of 1 mg protein/ml for the VLM, 4 mg protein/ml for the renal medulla, and 0.2 mg protein/ml for adrenomedullary cells. Assays were conducted in a total volume of 250 μl in polypropylene 96-well plates (Beckman Macrowell), and each well contained 125 μl membrane suspension, 25 μl radioligand, and 100 μl drug or vehicle. Incubations were initiated by the addition of membrane and were carried out for 30 min at 22° C. Nonspecific binding was defined in the presence of 10 μM BDF-6143, an imidazoline adrenergic agent. Specific $\alpha_2$-adrenergic binding was defined by inhibition with (−)epinephrine (0.1 mM). In experiments using catecholamines, all samples contained ascorbic acid in a final concentration of 0.001%. Incubations were terminated by vacuum filtration using a cell harvester (Brandel) equipped with Teflon tubing to reduce absorption of the radioligand over glass fiber filters (Schleicher & Schuell #34) which were preincubated for 4 h at 4° C. in 0.03% polyethylimine to reduce nonspecific binding to the filter. The filters were washed four times with 5 ml ice-cold Tris-HCl, placed in scintillation vials, covered with 4 ml scintillation cocktail (BioSafe II, Research Products International), and counted at 50% efficiency (Beckman LS5801). Protein was assayed by the bicinchoninic acid method.

Data were obtained as dpm and transferred to the Equilibrium Binding Data Analysis (EBDA) program for initial processing; 4 to 10 experiments were analyzed simultaneously by using the LIGAND program for nonlinear curve-fitting. Protein assay data were also analyzed by nonlinear curve-fitting.

[$^3$H]Clonidine (60-80 Ci/mmol) and [$^{125}$I]p-iodoclonidine (2200 Ci/mmol) were obtained from New England Nuclear (Boston, Mass.), stored at −20° C. in ethanol and diluted in water prior to assay. Stock solutions of both compounds were made in 0.01 M acetic acid up to one week prior to use. Epinephrine and clonidine were purchased from Sigma Chemical (St. Louis, Mo.). Cimetidine was purchased from Research Biochemicals International (Natick, Mass.).

Assays for measuring imidazoline receptor-mediated arachidonic acid release from PC12 cells is as described in Ernsberger et al., (1995, *FASEB J.* 9:A114).

6.1.4 Preparation of Antibodies

IAA-RP linked to KLH was prepared by first reacting disodium IAA-RP (11.1 μmol) with 10 mg of 1-ethyl-3-(3-dimethylaminopropyl)carbodiimide HCl (EDCI; Sigma) in 0.5 mL of acidified saline (pH 6). After 5 min this was mixed with freshly dialyzed KLH protein (0.5 mg in 0.5 ml of 10 mM phosphate buffered saline [PBS; pH 7.4]). The solution was incubated at room temperature for 5-7 h, then dialyzed repeatedly against PBS at 4° C. Five male mice were injected (approx. 0.2 ml i.p.) with 200-250 μg KLH linked to IAA-RP prepared in Freund's Complete Adjuvant in oil. Each mouse received booster injections (i.v.) of KLH-IAA-RP in PBS after 6 weeks and 18 weeks. Five days after the last injection, the mouse with highest IAA-RP antibody titer was anesthetized with ether, then bled. Whole blood was collected, allowed to clot, then centrifuged (3000 g). The untreated plasma was the source of polyclonal antibodies against IAA-RP (pAb-IAA-RP). The mouse was euthanized by cervical dislocation then underwent spleenectomy, for preparation of monoclonal antibodies.

IAA-RP (as well as IAA-R and numerous potential congeners and related imidazoles) was similarly linked to BSA (Sigma) as was done for KLH above. After dissolving in 0.15 M NaHCO$_3$, the solution was applied (approx. 0.5 μg/well) to 96 well plastic Maxisorp immunoplates (Nunc) for use in an Enzyme-Linked Immunosorbent Assay (ELISA) method. Solutions (100 μl) of pAb-IAA-RP (diluted up to 1:8000 in PBS) applied to treated ELISA plates containing bound BSA-IAA-RP were incubated for 60 min at 37° C. After washing (5 times with PBS), 100 μl of a second antibody (goat-antimouse; 1:1000 dilution in PBS/ 1% BSA) linked to peroxidase (Kirkegaard and Perry Labs, Inc.) was added to each well and incubated for 60 min at 37° C. After washing (5 times with PBS), 95 μl of peroxidase substrate solution, ABTS (Kirkegaard and Perry Labs, Inc.), was added to each well. Plates were incubated for 20 min-4 h at 37° C. Optical density was assayed at 414 nm using a Spectra Max UV/V spectrometer as the detector system.

6.2. Results

The data presented in FIG. 2, and Table 1 below, demonstrate that IAA-RP inhibits binding of labeled clonidine to bovine RVLM membranes.

TABLE 1

Binding parameters for IAA-RP inhibition of [$^{125}$I]p-iodoclonidine binding to bovine RVLM membranes

| Condition | Imidazoline I Sites | | $\alpha_2$-Adrenergic Sites | |
|---|---|---|---|---|
| | $K_i$ (nM) | Percent Sites | $K_i$ (μM) | Percent Sites |
| Control | 160 ± 38 | 71 ± 5 | 57 ± 33 | 29 ± 5 |
| With epinephrine | 100 ± 19 | 86 ± 4 | 60 ± 48 | 14 ± 4 |
| With cimetidine | | 0 ± 0 | 210 ± 32 | 100 ± 10 |

$K_i$ values are IAA-RP concentration in nM (imidazoline sites) or μM ($\alpha_2$-adrenergic sites)±the standard error of the estimate and were obtained by nonlinear curve-fitting to a two-component logistic equation. IAA-RP distinguished two populations of [$^{125}$I]p-iodoclonidine binding sites. Sites with a high affinity for IAA-RP represented 71% of the total sites in the control condition, increased to 86% after selective masking of $\alpha_2$-adrenergic receptors with epinephrine and were eliminated by the addition of cimetidine to mask imidazoline sites. Conversely, sites with a low affinity for IAA-RP were diminished in the presence of epinephrine, but were predominant in the presence of cimetidine. These data indicate that VLM imidazoline receptor sites have a high affinity for IAA-RP whereas $\alpha_2$-adrenergic receptors have low affinity.

Authentic IAA-RP and IAA-R were both able to displace [$^{125}$I-] p-iodoclonidine; IAA-RP had a >100-fold greater affinity than IAA-R. In addition, incubation of brain-derived CDS with exogenous phosphatase reduced the binding affinity of CDS to adrenomedullary cell membranes (FIG. 3). In addition, as demonstrated in FIG. 4, CDS activity derived from bovine brain extracts and synthetic IAA-RP, each stimulated release of arachidonic acid from PC-12 cells. This effect was blocked by the selective imidazoline I$_1$ antagonist, efaroxan. In addition, CDS activity was shown to stimulate the release of catecholamines from adrenal chromaffin cells. In experiments using insulinoma cells in culture (e.g., β-TC3 cells), it was also observed that IAA-RP was capable of stimulating insulin release indicating that such cells are responsive to IAA-RP.

7. EXAMPLE

Stimulation of Insulin Release from Pancreatic Cells by IAA-RP and IAA-R

The example described below demonstrates that IAA-RP (tele-linked) stimulated release of insulin from cultured insulinoma cells (β-TC3 cells), further indicating that IAA-RP is a CDS compound. Furthermore, it suggests a useful model system for assaying imidazoline induced changes in K$^+$ channel activity such as, for example, activation (i.e., closure) of K$^+$ ATP-sensitive channels and/or regulation of transmitter release in regions of the body other than the pancreas. Such assays provide useful model systems for studying the relationship between imidazolines, neuropsychiatric and neurodegenerative disorders, and cell pathology and death associated with potassium channel dysfunction can occur with K$^+$ ATP channels.

7.1. Materials and Methods

Islets of Langerhans from male Wistar rats were isolated by collagenase digestion in a medium of bicarbonate-buffered physiological saline solution containing 4 mM D-glucose and 1 mM CaCl$_2$. Islets were selected under a binocular dissecting microscope and were used within two hours of isolation. Islets from humans were isolated from heart-beating cadaver organ donors by collagenase digestion and density gradient centrifugation (Chan, S. L. F., et al., 1997, *Brit. J. Pharmacol.* 120:926-932).

Incubations were done in 96-well plates. Isolated islets were incubated in 100 μl buffer solution supplemented with bovine serum albumin in humidified air: CO$_2$ (95:5%) at 37° C. in the presence of test agents. To eliminate any potential alpha-2 responses, yohimbine (10 μM), a potent alpha2-adrenergic blocker, was included in all incubations. After 60 min incubation, samples of medium were removed for measurement of insulin release by radioimmunoassay using anti-bovine insulin antiserum. Presence of insulin in the test media were compared to controls; positive differences represented amounts of insulin released. In reversal experiments, diazoxide (e.g., 200 µM) was pre-incubated to block glucose-induced insulin release. In these studies, test reagents were used to determine if they were capable of overcoming diazoxide's inhibitory effects on K+ ATP channels, a well known action of imidazoline secretagogues in islet cells. For example, efaroxan (an inhibitor of I-1 responses in adrenal medullary cells) is a well known I-3 agonist, i.e., it stimulates (at 100 µM) release of insulin and overcomes diazoxide inhibition thus illustrating again the dictomy between $I_1$ and $I_3$ receptor subtypes.

7.2. Results

The tele-isomers of IAA-RP and IAA-R (FIG. 1) and some of its congeners were evaluated in isolated pancreatic beta-cells harvested from normal rats and humans after autopsy. In direct stimulation experiments in rats, the tele-isomers of IAA-RP and IAA-R were potent stimulants of insulin release; the magnitude of response was dose-dependent, oftentimes effective at concentrations as low as 10 nM. The pros-isomer of IAA-R likewise stimulated insulin release with effects similar to or even greater than that seen with tele IAA-RP. Furthermore, tele-linked IAA-RP and tele- and pros-IAA-R were each able to reverse the inhibitory action of diazoxide on glucose-induced insulin release.

Diazoxide opens ATP-sensitive $K^+$ channels; a common feature of imidazolines active at $K^+$ channels (in particular, pancreatic $I_3$ receptors) is that such imidazolines reverse effects of diazoxide (Morgan, N. G., et al., 1995, *Ann. N.Y. Acad. Sci.* 763:361-373; Chan, S. L. F., et al., 1997, *Brit. J. Pharmacol.* 120:926-932).

As demonstrated, the imidazoleacetic acid-linked ribotides and ribosides are potent stimulants at yet another group of imidazoline receptors, the $I_3$ subtypes. The $I_3$ subtypes are associated with insulin release, a response that may also be linked to $K^+$ ATP-sensitive channels. The latter are present in many tissues of the body, particularly in the brain. Since IAA-RP immunoreactive cells are particularly rich in selected regions of the brain (e.g., particularly in the RVLM region of the brainstem), it is likely that the imidazole-linked ribotides and ribosides and their congeners also affect $K^+$channels, for example $K^+$-ATP-sensitive channels, present in nervous tissue. Such localization in the VLM also appears to confirm that IAA-RP is a CDS.

8. EXAMPLE

Imidazoleactic Acid-Ribotide Activity

The data described below addresses the identification of the structure of the endogenous IAA-RP isomer, the ability of the latter to interact with I-Rs, and the physiological significance of such interaction(s).

8.1. Materials and Methods

Chemical synthesis. I-4-AA-RP-$Na_2$ and I-4-AA-R HCl (FIG. 1) was synthesized using a method described for I-5-AA-RP and I-5-AA-R (Matulic-Adamic, J. & Watanabe, K. A. (1991) *Kor. J. Med. Chem.* 1, 54-64). Prior to that report, the structures of even synthetic IAA-conjugates were unknown (Baddiley, J., Buchanan, J. G., Hayes, D. H. & Smith, P. A. (1958) *J. Chem. Soc.* 3743-3745; Bauer, H. (1962) *J. Org. Chem.* 27, 167-170).

Animal and tissue sources. Animal Care and Use Committees of the authors' institutions approved all animal experiments. Human pancreata were harvested from heart-beating cadaver organ donors with next of kin's consent. Sprague-Dawley (SD) rats were used in most studies. Spontaneously hypertensive (SH) rats were used in blood pressure and IAA-RP release studies. Animals were obtained commercially.

Identification of IAA-RP by HPLC. Bovine brain CDS (Piletz, J. E., Chikkala, D. N. & Ernsberger, P. (1995) *J. Pharmacol. Exp. Ther.* 272, 581-587), human CSF and rat brain extracts (Prell, G. D., Douyon, E., Sawyer, W. F. & Morrishow, A. M. (1996) *J. Neurochem.* 66, 2153-2159; Prell, G. D., Morrishow, A. M., Duoyon, E. & Lee, W. S. (1997) *J. Neurochem.* 68, 142-151) were eluted from Dowex-AG-acetate columns (1-3N acetic acid) and analyzed by HPLC (Carter, A. J. & Muller, R. E. (1990) *J. Chromatogr.* 527, 31-39). Authentic IAA-ribotides (FIG. 1) and biological samples, equilibrated with 10 mM $H_3PO_4$ (pH 2.85), were eluted with a 2.5-62% $KH_2PO_4$ buffer (750 mM, pH 4.4) gradient. Other endogenous imidazoles, nucleotides and nucleosides (e.g. IAA, IAA-riboside, AMP, ATP) have retention times different from IAA-ribotides or negligible absorbance at 220 nm. $A_{220\ nm}$ of both ribotide isomers correlated with quantity (0.02-20 µg; r=0.96, p<0.01); elution times differed by ~3 min.

Alkaline Phosphatase (alk-Pase) Hydrolysis of CDS. Since [$^3$H]IAA-ribotide produced in vivo was cleaved by alk-Pase (11), CDS was examined to determine whether it containsed a ribose-P. Samples containing 26.2U of CDS (Piletz, J. E., Chikkala, D. N. & Emsberger, P. (1995) *J. Pharmacol. Exp. Ther.* 272, 581-587) were incubated (4 h in 250 µl) with 20U of alk-Pase (Sigma) in: activation buffer (50 mM TRIS-HCl, 5 mM $MgCl_2$, pH 7.7, 37° C.), thermally inactivating (4° C.) medium, or alk-Pase inactivation buffer (5 mM EDTA). Samples were then assayed for CDS binding activity (Piletz, J. E., Chikkala, D. N. & Ernsberger, P. (1995) *J. Pharmacol. Exp. Ther.* 272, 581-587). (1U=amount of CDS that inhibits 50% of $I_1$R-specific [$^3$H]clonidine binding to bovine adrenal membranes. In this case, CDS displayed an $IC_{50}$ after a 26.2-fold dilution.)

Affinity-purified anti-IAA-RP antibodies (Abs). Anti-IAA-RP sera were raised in rabbits immunized with I-4-AA-RP linked to keyhole limpet hemocyanin using 1-ethyl-3-(3-dimethylaminopropyl) carbodiimide (EDC, Sigma). Cross-reactivities were eliminated by successive solid-phase adsorptions of serum with EDC-modified BSA, AMP-BSA, ATP-BSA and rat serum proteins. Purified Abs were obtained by affinity-chromatography using I-4-AA-RP bound to agarose.

Quantitative ELISA. Rat brain homogenates were boiled, cooled, and centrifuged. Supernatants, extracted with butanol:chloroform (Khandelwal, J. K., Prell, G. D., Morrishow, A. M. & Green, J. P. (1989) *J. Neurochem.* 52, 1107-1113; Prell, G. D., Douyon, E., Sawyer, W. F. & Morrishow, A. M. (1996) *J. Neurochem.* 66, 2153-2159; Prell, G. D., Morrishow, A. M., Duoyon, E. & Lee, W. S. (1997) *J. Neurochem.* 68, 142-151), were mixed with an equal volume of anti-IAA-RP Abs (3% BSA, 20 mM PBS). After incubation (37° C., 1 h), 4-100 µl samples were incubated (16 h, 4° C.) in plates coated with I-4-AA-RP-BSA. Wells were washed, reacted (37° C., 1 h) with peroxidase-labeled goat anti-rabbit Abs (KPL, Gaithersburg, Md.), washed again, then developed with ABTS or TMB substrates (KPL). I-4-AA-RP levels were estimated from standard inhibition curves (1 pmol-10 nmol). Controls included samples devoid of I-4-AA-RP, anti-I-4-AA-RP sera, or secondary antibody. To study IAA-RP released from $P_2$ preparations (0.08-20 pmol), protein-free supernatants (10% TCA) and biotinylated goat anti-rabbit antibodies and peroxidase-streptavidin were used.

Immunocytochemistry. Anesthetized rats were perfused transcardially with 100 ml PBS (RT), 100 ml 4% EDC in PBS (RT), then 300 ml 4% paraformaldehyde (4° C.). Brains were post-fixed (2 h, 4% paraformaldehyde). Vibratome sections (50 μ) were pre-treated with 0.3% $H_2O_2$, rinsed with PBS, blocked in 5% normal goat serum (1 h) and then incubated with affinity-purified anti-IAA-RP Abs. Control sections received pre-immune serum, Abs pre-absorbed with I-4-AA-RP or no primary Abs. After 16 h at 4° C., sections were washed and stained (Vectastain Elite; Vector Labs, Burlingame, Calif.) using diaminobenzidine (0.5 mg/ml, 10 mM TRIS, pH 8.0, 0.01% $H_2O_2$), osmicated (0.1% $OsO_4$, 30 sec), rinsed and mounted.

Competition binding assays. Bovine adrenal medulla or RVLM membranes were suspended in TRIS buffer (5 mM, pH 7.7, with EDTA, EGTA and $MgCl_2$, all 500 μM) (0.2-1 mg protein/ml) and labeled with 0.5 nM [$^3H$]clonidine or 1 nM [$^{125}I$]p-iodoclonidine (PIC), respectively (Ernsberger, P., Piletz, J. E., Graff, L. M. & Graves, M. E. (1995) Ann. N.Y. Acad. Sci. 763, 163-168). Since the RVLM contains I-Rs and $α_2$Rs, an imidazoline/adrenergic agent, BDF-6143 (10 μM) (Göthert, M., Moldering, G. J., Fink, K. & Schlicker, E. (1995) Ann. NY. Acad. Sci. 763, 405-419), was used to assess total binding. Specific binding to $α_2$Rs or I-Rs was defined by inhibition with (–)epinephrine (100 μM) or cimetidine (10 μM), respectively. The latter was also used with adrenal membranes. Ascorbic acid (1 mg %) was used in studies with catecholamines. Incubations were stopped by vacuum filtration over pre-washed (TRIS-HCl) glass filters. Captured $^3H$ and $^{125}I$, were then measured by liquid scintillation. Results were analyzed using non-linear regression (PRISM, GraphPad). $K_1$ values were assessed using a two-component logistic equation.

$I_1R$ model: [$^3H$]Arachidonic acid (AA) release from PC-12 cells. Assays (Emsberger, P. (1998) J. Auton. Nerv. Syst. 72, 147-154 Ernsberger, P. (1998) J. Auton. Nerv. Syst. 72, 147-154) were done after a 30 min washout to attain a stable background. Cells were superfused with 0.01% BSA in Krebs buffer for seven 1-min fractions (baseline), then treated with 10 μM or 100 μM I-4-AA-RP alone, or together with efaroxan (10 μM), a prototypical $I_1$-antagonist/$I_3$-agonist. Controls included baseline release with vehicle alone (0-7 min) or vehicle containing efaroxan (5 min) before adding I-4-AA-RP. [$^3H$]products (>98% AA) collected in each 1-min fraction were expressed as fractional release defined as % total radioactivity incorporated into cells, corrected for [$^3H$]AA previously released (Ernsberger, P. (1998) J. Auton. Nerv. Syst. 72, 147-154).

$I_3R$ model: Insulin release from pancreas (Eglen, R. M., Hudson, A. L., Kendall, D. A., Nutt, D. J., Morgan, N. G., Wilson, V. G. & Dillon, M. P. (1998) TIPS 19, 381-390; Chan, S. L. F. (1998) Gen. Pharmacol. 31, 525-529; Morgan, N. G. (1999) Exp. Opin. Invest. Drugs 8, 575-584). Islets of Langerhans from male Wistar rats or human pancreata were isolated by collagenase digestion. Hand-picked islets were incubated in $NaHCO_3$-buffered saline containing 1 mM $CaCl_2$, 1 mg/ml BSA and test reagents. After incubation, insulin levels in supernatants were analyzed by RIA. The $I_3$-blocker, KU-14R, served to verify $I_3R$ function.

$Ca^{++}$ dependent IAA-ribotide release. Synaptosome and vesicle-enriched $P_2$ fractions (Whittaker, V. P., Michaelson, I. A. & Kirkland, R. J. A. (1964) Biochem. J. 90, 293-303), each pooled from 2 SH rat brains (Arneric, S. P., Giuliano R., Emsberger, P., Underwood, M. D. & Reis, D. J. (1990) Brain Res. 511, 98-112), were suspended in Krebs buffer (KrB) saturated with 95% $O_2$/5% $CO_2$, divided into 0.5 ml aliquots, and mixed with 0.5 ml of either: i) KrB, or ii) KrB without $Ca^{++}$containing 55 mM $K^+$ (to depolarize cells) and EDTA (to chelate endogenous $Ca^{++}$), or iii) KrB with 55 mM $K^+$ (release buffer). I-4-AA-RP was measured (ELISA) after incubation (10 min, 37° C.). Release was expressed as % of controls: [IAA-RP in release media/mean of the two non-release controls in each experiment (N=5)]×100. Results were analyzed by two-way repeated measures ANOVA for values that exceeded controls and by Wilcoxon's test.

Effects of ribotide on mean arterial pressure (MAP) and heart rate (HR). Bilateral I-4-AA-RP microinjections (60 nl, 100 nmol) into the RVLM of SH rats were performed (Emsberger, P. & Haxhiu, M. A. (1997) Am. J. Physiol. 273, R1572-R1579) after the sympatho-excitatory area was confirmed by showing glutamate-induced MAP elevation $\geq 30$ mm Hg. MAP and HR values were measured every 5 min. After each experiment, the injection site was marked by infusion of rhodamine microspheres. Changes were assessed relative to baseline values by two-way repeated measures ANOVA and Dunnett's test. A second group of SH rats (injection controls) received vehicle injections to control for injection effects and for volume artifacts due to multiple injections. Vehicle contained 2 nmol rilmenidine, a sub-threshold dose, far below that known to cause any detectable effect (Gomez, R. E., Emsberger, P., Feinland, G. & Reis, D. J. (1991) Eur. J. Pharmacol. 195, 181-191). In a follow-up study, SH rats (N=6) were given I-4-AA-RP then moxonidine. When used alone, it reduces MAP to normotensive levels (Emsberger, P., Elliott, H. L., Weimann, H.-J., Raap, A., Haxhiu, M. A., Hofferber, E., Low-Kroger, A., Reid, J. L. & Mest, H. J. (1993) Cardiovas. Drug Rev. 11, 411-431).

8.2. Results

I-4-AA-RP is the endogenous isomer. HPLC analysis showed that addition of either I-4-AA-RP or I-5-AA-RP to test samples produced nearly quantitative $A_{220\ nm}$ peak-area recoveries. All biological samples (FIG. 5) displayed peaks indicative of I-4-AA-RP. $A_{220}$ of the latter increased in samples mixed with synthetic I-4-AA-RP (50-200 ng, FIG. 5C, F), while a novel peak appeared in samples mixed with I-5-AA-RP (FIG. 5D). This demonstrates that the I-4-AA-RP isomer (FIG. 1, hereafter denoted as "IAA-RP") is present in tissues (FIG. 5) and in CSF (not shown). Its endogenous metabolite is therefore I-4-AA-R, hereafter denoted "IAA-R." The latter has also been found in rat and human samples using GC/MS.

Specificity of anti-IAA-RP Abs and quantitative ELISA. Purified anti-IAA-RP Abs had negligible cross-reactivity with >50 compounds (10 nM-0.1 mM), including free and BSA-conjugated imidazoles such as IAA-R, I-5-AA-RP, I-5-AA-R, IAA, related endogenous and synthetic pyrimidine- and purine-ribose-Ps (e.g. ZMP, AMP, ADP, ATP, cAMP, cGMP), unconjugated compounds such as histidine and histamine and their metabolites. Others included phosphatase and 5'nucleotidase inhibitors and compounds relevant to the imidazol(in)e field, e.g. clonidine, cimetidine, efaroxan, KU-14R, agmatine and idazoxan. Abs did not stain Western blots of rat brain homogenates.

Quantitative ELISA confirmed that rat brain extracts contained IAA-RP (1.1±0.6 μg/g tissue, N=8).

IAA-RP is present in brainstem neurons. RVLM neurons stained intensely in sections reacted with anti-IAA-RP Abs (FIG. 6A). Neuropil staining due to the presence of IAA-RP in neuronal processes was also apparent. Myelinated axon bundles were unstained (FIG. 6). Adjacent sections treated with primary Abs pre-absorbed with IAA-RP (FIG. 6B), pre-immune serum, or with secondary Abs (horse anti-rabbit) alone showed no appreciable immunoreactivity. Neuronal staining was present in other brainstem areas, e.g. the solitary, gracile, vestibular, ventral cochlear, medial parabrachial and inferior olivary nuclei, and Purkinje cell somata and dendrites of the cerebellar cortex.

Alk-Pase depleted CDS activity. Treatment with active alk-Pase decreased CDS activity (FIG. 3) from 26.2U to 6.7U (−74%); inactivated enzyme had no effect. Therefore a substance containing a hydrolysable P-monoester appeared to mediate most of the CDS activity (Piletz, J. E., Chikkala, D. N. & Ernsberger, P. (1995) *J. Pharmacol. Exp. Ther.* 272, 581-587) consistent with conversion of IAA-RP to IAA-R.

IAA-RP binds to adrenal medulla $I_1R$ sites and is an $I_1R$-agonist in PC12 cells. The adrenal does not express $\alpha_2$-sites and is a model for $I_1R$ binding (Ernsberger, P. (1998) *J. Auton. Nerv. Syst.* 72, 147-154 Ernsberger, P. (1998) *J. Auton. Nerv. Syst.* 72, 147-154; Ernsberger, P., Piletz, J. E., Graff, L. M. & Graves, M. E. (1995) *Ann. N.Y. Acad. Sci.* 763, 163-168). In this tissue, IAA-RP and IAA-R displaced [$^3$H]clonidine with affinities ($K_1$ values) of 13±2 μM and 24±5 μM, respectively. [$^3$H]AA release was studied in PC12 cells, which derive from an adrenal medullary tumor and, like the adrenal, express $I_1Rs$ but not $\alpha_2Rs$ and are a model for $I_1R$ responses (Emsberger, P. (1998) *J. Auton. Nerv. Syst.* 72, 147-154; Emsberger, P. (1998) *J. Auton. Nerv. Syst.* 72, 147-154.). IAA-RP caused a dose-related stimulation of [$^3$H]AA release. IAA-RP at 10 μM increased release by 68±29% (FIG. 4, p<0.05; N=13); 100 μM elicited a larger response (177±89%; p<0.05, N=6; not shown). In contrast, IAA-R (10 μM-1 mM) showed no significant response. The $I_1$-antagonist/$I_3$-agonist efaroxan abolished responses to IAA-RP (FIG. 4).

IAA-RP is an $I_3R$ agonist. Potentiation of glucose-induced insulin release is the best-characterized $I_3R$-mediated response (Eglen, R. M., Hudson, A. L., Kendall, D. A., Nutt, D. J., Morgan, N. G., Wilson, V. G. & Dillon, M. P. (1998) *TIPS* 19, 381-390; Chan, S. L. F. (1998) *Gen. Pharmacol.* 31, 525-529; Morgan, N. G. (1999) *Exp. Opin. Invest. Drugs* 8, 575-584). As reported for CDS and other $I_3R$-agonists (Chan, S. L. F. (1998) *Gen. Pharmacol.* 31, 525-529; Morgan, N. G. (1999) *Exp. Opin. Invest. Drugs* 8, 575-584; Chan, S. L. F., Atlas, D., James, R. F. L. & Morgan, N. G. (1997) *Br. J. Pharmacol.* 120, 926-932). IAA-RP increased insulin secretion from islets (FIG. 7). It also overcame inhibitory effects of the $K_{ATP}$-channel agonist, diazoxide (FIG. 7A-C). These IAA-RP effects are characteristic of $I_3R$ agonists but, significantly, IAA-RP was far more potent than efaroxan (FIG. 7A), the prototypical $I_3$-agonist/$I_1$-antagonist. IAA-RP stimulation was biphasic in rat (FIG. 7B) and human islets. In rats, IAA-RP had an $EC_{50}$ of 30-50 nM. Human islets appeared to be even more sensitive, displaying an $EC_{50}$ of ~3 nM. The $I_3R$ antagonist KU-14R (Chan, S. L. F. (1998) *Gen. Pharmacol.* 31, 525-529) abolished IAA-RP-induced secretion (FIG. 7C), confirming $I_3R$ activity.

IAA-RP has high affinity for brainstem I-R sites. In the RVLM, [$^{125}$I]PIC labels both I-R and $\alpha_2$-sites (Ernsberger, P., Piletz, J. E., Graff, L. M. & Graves, M. E. (1995) *Ann. N. Y. Acad. Sci.* 763, 163-168). Competition curves for IAA-RP (FIG. 2) were biphasic, consisting of both high and low affinity sites. In the absence of I-R and $\alpha_2$-masking ligands, the high affinity component comprised 71±5% (X±SEM) of total binding ($K_1$ 160±38 nM). The remaining sites showed >300-fold lower affinity for IAA-RP ($K_1$ 57±33 μM). After masking $\alpha_2Rs$ with epinephrine, IAA-RP high affinity binding accounted for 86±4% of total binding ($K_1$ 100±19 nM); the $K_1$ of low affinity sites was 60±48 μM. Conversely, when I-sites were masked with the imidazole cimetidine, IAA-RP high affinity binding was abolished and only low affinity sites remained (presumably $\alpha_2$-Rs; $K_1$ 210±32 μM). Thus, in the RVLM, IAA-RP exhibited high affinity for I-R sites and was >1000-fold more selective for I-Rs than for $\alpha_2$-sites. In parallel assays, IAA-R had very low affinity ($K_1$ 266±48 μM; not shown).

IAA-RP shows $Ca^{++}$-dependent release from neuronal terminals. IAA-RP release from $P_2$ nerve endings was studied. IAA-RP levels in controls showed little variation (≦11%) within each preparation, but varied considerably among preparations (5.7-35.5 fmol/μl). Nevertheless, a significant net effect was observed (p<0.05, ANOVA). Mean IAARP release in samples containing $Ca^{++}$ exceeded by 40.3% (p=0.03 Wilcoxon) the mean (and the median by 49%) of controls grouped together (X±SEM: 22.7±4.8 fmol/μl) (i.e. non-depolarized preparations or those deprived of $Ca^{++}$ by EDTA). These data demonstrate that IAA-RP is stored in fractions that contain synaptic endings and IAA-RP undergoes depolarization-induced release consistent with trans-synaptic function.

Microinjection of IAA-RP into the RVLM produces hypertension. SH rats were used as a model system (Ernsberger, P., Elliott, H. L., Weimann, H.-J., Raap, A., Haxhiu, M. A., Hofferber, E., Low-Kroger, A., Reid, J. L. & Mest, H. J. (1993) *Cardiovas. Drug Rev.* 11, 411-431) since IAA-RP, as an $I_1$-agonist (FIG. 4), was expected to lower MAP. Yet, IAA-RP immediately raised MAP an average of ~25 mm Hg over baseline (FIG. 8A; p<0.01, ANOVA; N=6). A second microinjection 20 min later again raised MAP (FIG. 8A; p<0.05). In contrast, HR showed no significant changes. IAA-R (100 nmol; N=3, not shown) did not alter MAP or HR significantly. Injection alone (injection controls) did not alter HR or MAP (FIG. 8B), confirming that MAP elevations were due to IAA-RP. In a smaller study using normotensive rats (N=3), IAA-RP produced a similar hypertensive response. To assess if IAA-RP's effect could be reversed, the $I_1$-agonist moxonidine (MOX; 4 nmol) was microinjected into SH rats whose MAP had been elevated (20.4±5.6% above baseline) following six-100 nmol doses of IAA-RP. MOX completely reversed IAA-RP's effect and lowered MAP (37.3±6.3%) towards normotensive levels within 30 min. This further suggests that IAA-RP's hypertensive effect was not mediated by $I_1Rs$.

HPLC studies (FIG. 5) of tissue extracts revealed the biological isomer to be I-4-AA-RP (FIG. 1). Its presence in brainstem regions and, in particular, in the RVLM (FIG. 6) is significant, since this region is an important site of action for a class of antihypertensive agents which are thought to exert their effects via $I_1Rs$ (Emsberger, P. & Haxhiu, M. A. (1997) *Am. J. Physiol.* 273, R1572-R1579;Gomez, R. E., Emsberger, P., Feinland, G. & Reis, D. J. (1991) *Eur. J. Pharmacol.* 195, 181-191;Ernsberger, P., Elliott, H. L., Weimann, H.-J., Raap, A., Haxhiu, M. A., Hofferber, E., Low-Kroger, A., Reid, J. L. & Mest, H. J. (1993) *Cardiovas. Drug Rev.* 11, 411-431; Chan, S. L. F., Atlas, D., James, R. F. L. & Morgan, N. G. (1997) *Br. J. Pharmacol.* 120, 926-932). Several observations indicate that IAA-RP is an I-R agonist. Firstly, IAA-RP bound to prototypical $I_1Rs$ in adrenal tissue and promoted AA release from PC12 cells (FIG. 4). Secondly, IAA-RP induced a robust stimulatory response in pancreatic islets (FIG. 7), consistent with $I_3R$ activity. In fact, IAA-RP was unusually potent ($EC_{50}$: 30-50 nM, FIG. 7B) in comparison to efaroxan, the prototypical $I_3$-agonist which typically shows maximal stimulation at ~100 μM (Chan, S. L. F. (1998) *Gen. Pharmacol.* 31, 525-529; Chan, S. L. F. & Morgan, N. G. (1990) *Eur. J. Pharmacol.* 176, 97-101). Notably, similar responses are elicited by CDS (Chan, S. L. F. (1998) *Gen. Pharmacol.* 31, 525-529;Chan, S. L. F., Atlas, D., James, R. F. L. & Morgan, N. G. (1997) *Br. J. Pharmacol.* 120, 926-932), a putative but unidentified endogenous I-R ligand. Since our CDS preparation contained IAA-RP (FIG. 5), and alk-Pase abolished most of CDS's activity (FIG. 3), we surmise that CDS I-R activity might derive from IAA-RP. Historically, CDS was first shown to displace clonidine from $\alpha_2$Rs (Regunathan, S. & Reis, D. J. (1996) *Ann. Rev. Pharmacol. Toxicol.* 36, 511-544; Eglen, R. M., Hudson, A. L., Kendall, D. A., Nutt, D. J., Morgan, N. G., Wilson, V. G. & Dillon, M. P. (1998) *TIPS* 19, 381-390;Meeley, M. P., Emsberger, P., Granata, A. R. & Reis, D. J. (1986) *Life Sci.* 38, 1119-1126; Atlas, D. (1991) *Biochem. Pharmacol.* 41, 1541-1549; Grigg, M., Musgrave, I. F. & Barrow, C. J. (1998) *J. Auto. Nerv. Sys.* 72, 86-93; Parker, C. A., Hudson, A. L., Nutt, D. J., Dillon, M. P., Eglen, R. M., Chan, S. L. F., Morgan, N. G. & Crosby, J. (1999) *Eur. J. Pharmacol.* 378, 213-221; Singh, G., Hussain, J. F., MacKinnon, A., Brown, C. M., Kendall, D. A. & Wilson, V. G. (1995) *N.-S. Arch. Pharmacol.* 351, 17-26). Thus, if IAA-RP is an/the active factor in CDS, then it might also be expected to act at $\alpha_2$Rs. IAA-RP's biphasic response (FIG. 7B) in islets provides physiological evidence consistent with the possibility that sub-μM levels of IAA-RP stimulate insulin release, while higher levels are inhibitory, responses expected with α2 R-stimulation. Considering that IAA-RP affinity for I-R vastly exceeds that for $\alpha_2$-sites (FIG. 2), the stimulatory phase can be explained by I-R activation while the inhibition may be due to $\alpha_2$R activation (Morgan, N. G. (1999) *Exp. Opin. Invest. Drugs* 8, 575-584).

Some of the observations decribed herein were unexpected since, as an $I_1$-agonist (FIG. 4), IAA-RP injection into the RVLM was expected to lower blood pressure, as observed with other $I_1$-agonists (Emsberger, P. & Haxhiu, M. A. (1997) *Am. J. Physiol.* 273, R1572-R1579; Ernsberger, P., Elliott, H. L., Weimann, H.-J., Raap, A., Haxhiu, M. A., Hofferber, E., Low-Kroger, A., Reid, J. L. & Mest, H. J. (1993) *Cardiovas. Drug Rev.* 11, 411-431). Instead, as was observed with CDS (Atlas, D. (1991) *Biochem. Pharmacol.* 41, 1541-1549.). IAA-RP produced a rapid, transient increase in MAP (FIG. 8A), despite possible ceiling effects after using SH rats. These observations led to reconsideration of the actions of I-Rs within the RVLM where I-R activity has been attributed to $I_1$-sites since its pharmacological profile was consistent with that of $I_1R$ models (Ernsberger, P. (1998) *J. Auton. Nerv. Syst.* 72, 147-154 Ernsberger, P. (1998) *J. Auton. Nerv. Syst.* 72, 147-154; Emsberger, P. (1998) *J. Auton. Nerv. Syst.* 72, 147-154 Ernsberger, P. (1998) *J. Auton. Nerv. Syst.* 72, 147-154; Emsberger, P. & Haxhiu, M. A. (1997) *Am. J. Physiol.* 273, R1572-R1579). The most direct explanation for the observed results is that the RVLM contains two cimetidine-sensitive I-R subtypes, $I_1$Rs and an undefined I-R subtype, which regulate blood pressure in a reciprocal manner. This contention is supported by the fact that the IAA-RP binding profile in the RVLM (which exhibits both high and low affinity sites (FIG. 2) differs markedly from that of the single site observed in adrenal tissue, which contains prototypical $I_1R$ sites. Affinities of high-affinity sites were >100-fold greater than those of both low-affinity RVLM sites and adrenal $I_1R$ sites. Furthermore, when ratios of affinities of the IAA-RP and IAA-R pair were considered, the $K_1$ (IAA-RP, low-affinity)/$K_1$ (IAA-R) ratio in the RVLM was nearly the same as the $K_1$ (IAA-RP)/$K_1$(IAA-R) ratio in adrenal tissue. Yet, both ratios were orders of magnitude different from the $K_1$ (IAA-RP, high-affinity)/$K_1$(IAA-R) ratio in the RVLM. Taken together, the data suggest that in the RVLM the low affinity site is $I_1$R-like and that IAA-RP's hypertensive effect (FIG. 8) derives from a non-$I_1$R, high-affinity site. Although the nature of this putative I-R is unknown, we note that the $K_1$ of the high-affinity site (100 nM, FIG. 2) appears to be congruent with its $EC_{50}$ at $I_3$Rs (30-50 nM, FIG. 7B), and that the $I_3$-agonist efaroxan also induces hypertension when injected into the RVLM (Emsberger, P. (1998) *J. Auton. Nerv. Syst.* 72, 147-154 Emsberger, P. (1998) *J. Auton. Nerv. Syst.* 72, 147-154; Ernsberger, P., Piletz, J. E., Graff, L. M. & Graves, M. E. (1995) *Ann. N.Y. Acad. Sci.* 763, 163-168). Since there is evidence that, in islets, $I_3$-agonists interact with K+ ATP channels (Chan, S. L. F. (1998) *Gen. Pharmacol.* 31, 525-529; Morgan, N. G. (1999) *Exp. Opin. Invest. Drugs* 8, 575-584), that the latter are abundant in the RVLM (Golanov, E. V. & Reis, D. J. (1999) *Brain Res.* 827, 210-214), and that imidazol(in)e-induced closure of K+ ATP channels promotes neuronal excitability (Chan, S. L. F., Atlas, D., James, R. F. L. & Morgan, N. G. (1997) *Br. J. Pharmacol.* 120, 926-932), we hypothesize that a site(s) related to these channels may mediate the effects of IAA-RP. Thus, the proposition that IAA-RP might act via $I_3$-like-Receptors in the midbrain or separate potassium channels merits further consideration.

The data described herein suggest that IAA-RP may participate in trans-synaptic signaling in brain, since it exists in brainstem neurons (FIG. 6), exhibits depolarization-induced $Ca^{++}$-dependent release from $P_2$ synaptosomal elements, has relatively high affinity for membrane-bound I-R sites (FIG. 2), and produces physiological effects upon exogenous application (FIG. 8A). IAA-RP is rapidly metabolized by phosphatases and ecto-5'nucleotidases (Thomas, B. & Prell, G. D. (1995) *J. Neurochem.* 65, 818-826, Crowley, G. M. (1964) *J. Biol. Chem.* 239, 2593-2601) (GDP, unpub.), both membrane-bound, to produce IAA-R, which has far less activity than IAA-RP. This would be compatible with a mechanism for rapid removal of IAA-RP so as to regulate its synaptic levels. In the RVLM, accumulation of IAA-R may also block I_R activation by IAA-RP. Collectively, these observations meet the major requirements (Erulkar, S. D. (1994) in Basic Neurochemistry, eds. Siegel, G. J., Agranoff, B. W., Albers, R. W. & Molinoff, P. B. (Raven Press, New York), pp. 181-208) to indicate that IAA-RP is a neurotransmitter. Thus, one can speculate how IAA-RP might tonically over-stimulate brainstem I-Rs to produce hypertension. The potent stimulation of insulin release by IAA-RP, its ability to induce AA release and the IAA-R's presence in plasma and urine (Tabor, H. & Hayaishi, O. (1955) *J. Amer. Chem. Soc.* 77, 505-506; Schayer, R. W. (1959) *Physiol. Rev.* 39, 116-126; Green, J. P., Prell, G. D., Khandelwal, J. K. & Blandina, P. (1987) *Agents Actions* 22, 1-15; Karjala, S. A. (1955) *J. Amer. Chem. Soc.* 77, 504-505), also suggest that IAA-RP might exert hormone-like activity in the periphery. Indeed, IAA-RP's actions in the RVLM and in the pancreas reported here suggest it could be a link connecting the disorders of hypertension and diabetes (Bousquet, P., Feldman, J. & Schwartz, J. (1984) *J. Pharmacol. Exp. Ther.* 230, 232-236; Chan, S. L. F. (1998) *Gen. Pharmacol.* 31, 525-529; Morgan, N. G. (1999) *Exp. Opin. Invest. Drugs* 8, 575-584; Emsberger, P. & Haxhiu, M. A. (1997) *Am. J. Physiol.* 273, R1572-R1579).

It is possible that different preparations of CDS (Regunathan, S. & Reis, D. J. (1996) *Ann. Rev. Pharmacol. Toxicol.* 36, 511-544; Meeley, M. P., Emsberger, P., Granata, A. R. & Reis, D. J. (1986) *Life Sci.* 38, 1119-1126; Atlas, D. (1991) *Biochem. Pharmacol.* 41, 1541-1549; Grigg, M., Musgrave, I. F. & Barrow, C. J. (1998) *J. Auto. Nerv. Sys.* 72, 86-93; Parker, C. A., Hudson, A. L., Nutt, D. J., Dillon, M. P., Eglen, R. M., Chan, S. L. F., Morgan, N. G. & Crosby, J. (1999) *Eur. J. Pharmacol.* 378, 213-221; Singh, G., Hussain, J. F., MacKinnon, A., Brown, C. M., Kendall, D. A. & Wilson, V. G. (1995) *N.-S. Arch. Pharmacol.* 351, 17-26, Piletz, J. E., Chikkala, D. N. & Ernsberger, P. (1995) *J. Pharmacol. Exp. Ther.* 272, 581-587) may contain variable amounts of IAA-RP and/or other potentially active substances (possibly hormone) (Musgrave, I. F. & Badoer, E. (2000) *Br. J. Pharmacol.* 129, 1057-105). Nevertheless, the data described herein provides evidence that IAA-RP has a hitherto unrecognized physiological and/or patho-physiological function in the CNS and periphery.

The present invention is not to be limit in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

I claim:

1. An antibody which immunospecifically binds to a compound selected from the group consisting of an imidazoleacetic acid-ribotide and an imidazoleacetic acid-riboside.

2. An antibody prepared by immunizing a subject with an immunogen comprising a compound of formula:

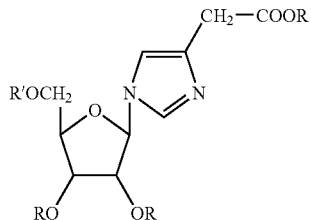

where R is hydrogen and $R^1$ can be hydrogen or $PO_3H_2$.

* * * * *